US011180797B2

(12) United States Patent
Gines et al.

(10) Patent No.: US 11,180,797 B2
(45) Date of Patent: Nov. 23, 2021

(54) MOLECULAR COMPUTING COMPONENT AND METHOD OF MOLECULAR COMPUTING

(71) Applicants: THE UNIVERSITY OF TOKYO, Tokyo (JP); CENTRE NATIONAL DE LA RECHERCHE SCIENTIFIQUE (CNRS), Paris (FR)

(72) Inventors: Guillaume Gines, Tokyo (JP); Yannick Rondelez, Tokyo (JP); Teruo Fujii, Tokyo (JP)

(73) Assignees: THE FOUNDATION FOR THE PROMOTION OF INDUSTRIAL SCIENCE, Tokyo (JP); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 119 days.

(21) Appl. No.: 15/998,743

(22) PCT Filed: Feb. 16, 2016

(86) PCT No.: PCT/IB2016/000419
§ 371 (c)(1),
(2) Date: Aug. 16, 2018

(87) PCT Pub. No.: WO2017/141068
PCT Pub. Date: Aug. 24, 2017

(65) Prior Publication Data
US 2020/0172967 A1 Jun. 4, 2020

(51) Int. Cl.
*C12Q 1/68* (2018.01)
*C12Q 1/6844* (2018.01)

(52) U.S. Cl.
CPC ...... *C12Q 1/6846* (2013.01); *C12Q 2521/101* (2013.01); *C12Q 2521/301* (2013.01); *C12Q 2521/319* (2013.01); *C12Q 2565/537* (2013.01)

(58) Field of Classification Search
None
See application file for complete search history.

(56) References Cited

U.S. PATENT DOCUMENTS

2011/0136104 A1* 6/2011 Pregibon .............. C12Q 1/6851
435/6.12

OTHER PUBLICATIONS

Baccouche et al., Dynamic DNA-toolbox reaction circuits: A walk-through, Methods, May 15, 2014;67(2):234-49. doi:10.1016/j.ymeth.2014.01.015. Epub Feb. 2, 2014.*

(Continued)

*Primary Examiner* — Aaron A Priest
(74) *Attorney, Agent, or Firm* — Foley & Lardner LLP; Sunit Talapatra

(57) ABSTRACT

An object is to provide a component for molecular Computing and a method of molecular Computing. A component for molecular Computing, the component comprising: a microsphere including pores, at least some of which are open on a surface of the microsphere, and a plurality of modules grafted on the microsphere wherein each of the modules is a continuous séquence of nucleic acid base. A method of molecular Computing with a component comprising a microsphere including pores, at least some of which are open on a surface of the microsphere, and a plurality of modules grafted on the microsphere wherein each of the modules is a DNA strand, the method comprising steps of: designing the modules to create a molecular program! attaching the modules to the microsphere! bringing the microsphere into contact with a solution containing a mixture of enzymes! and incubating the microsphere with (Continued)

the modules at a constant température so that DNA production and exchange happen locally between the grafted modules according to the molecular program.

12 Claims, 22 Drawing Sheets

(56) References Cited

OTHER PUBLICATIONS

Aubert et al., Computer-assisted design for scaling up systems based on DNA reaction networks, J R Soc Interface. Apr. 6, 2014; 11 (93): 20131167. doi: 10.1098/rsif.2013.1167.*
Milligan et al., Using RecA protein to enhance kinetic rates of DNA circuits, Chem Commun (Camb), Jun. 11, 2015;51 (46):9503-6. doi: 10.1039/c5cc02261d.*
Adessi et al., "Solid phase DNA amplification: characterization of primer attachment and amplification mechanism", Nucleic Acids Research, 2000, vol. 28, No. 20, e87.
Aubert et al. "Computer-assisted design for scaling up systems based on DNA reaction networks", Journal of the Royal Society, vol. 11, 2013, pp. 1-12.
Ayukawa et al., "RTRACS: A Modularized RNA-Dependent RNA Transcription System with High Programmability", Accounts of Chemical Research, vol. 44, No. 12, 2011, pp. 1369-1379.
Baccouche et al., "Dynamic DNA-toolbox reaction circuits: A walkthrough", Methods, vol. 67, 2014, pp. 234-249.
Barawkar et al., "Synthesis, biophysical properties, and nuclease resistance properties of mixed backbone oligodeoxynucleotides containing cationic internucleoside guanidinium linkages: Deoxynucleic guanidine/DNA chimeras", Proc. Natl. Acad. Sci. USA, vol. 95, p. 11047-11052, Sep. 1998.
Bartosik et al., "Magnetic bead-based hybridization assay for electrochemical detection of microRNA", Analytica Chimica Acta, vol. 813, 2014, pp. 35-40.
Behlke, "Chemical Modification of siRNAs for In Vivo Use", Oligonucleotides, vol. 18, pp. 305-320, 2008.
Boado et al., "Complete Protection of Antisense Oligonucleotides against Serum Nuclease Degradation by an Avidin-Biotin System", Bioconjugate Chem., 1992, vol. 3, pp. 519-523.
Chou et al., "Porous Bead-Based Diagnostic Platforms: Bridging the Gaps in Healthcare", Sensors, 2012, vol. 12, p. 15467-15499.
Chrisey et al., "Covalent attachment of synthetic DNA to self-assembled monolayer films", Nucleic Acids Research, 1996, vol. 24, No. 15, pp. 3031-3039.
Cardic et al., "Substitution of 3-Phosphate Cap with a Carbon-Based Blocker Reduces the Possibility of Fluorescence Resonance Energy Transfer Probe Failure in Real-Time PCR Assays", Clinical Chemistry, vol. 50, No. 6, 2004, pp. 1080-1082.
Dias et al., "Antisense Oligonucleotides: Basic Concepts and Mechanisms", Molecular Cancer Therapeutics, vol. 1, Mar. 2002, pp. 347-355.
Dinh et al.,"An Effective Method for Evolving Reaction Networks in Synthetic Biochemical Systems", IEEE Transactions On Evolutionary Computation, vol. 19, No. 3, Jun. 2015, pp. 374-386.
Dressman et al., "Transforming single DNA molecules into fluorescent magnetic particles for detection and enumeration of genetic variations", PNAS, vol. 100, No. 15, Jul. 22, 2003, pp. 8817-8822.
Fan et al., "Dynamic DNA Hybridization on a Chip Using Paramagnetic Beads", Anal. Chem., vol. 71, 1999, pp. 4851-4859.
Ferguson et al., "High-Density Fiber-Optic DNA Random Microsphere Array", Anal. Chem., vol. 72, 2000, pp. 5618-5624.
Fujii et al., "Predator-Prey Molecular Ecosystems", ACSNANO, vol. 7, No. 1, pp. 27-34, 2013.
Gines et al., "A multiplex assay based on encoded microbeads conjugated to DNA NanoBeacons to monitor base excision repair activities by flow cytometry", Biosensors and Bioelectronics, vol. 58, 2014, pp. 81-84.

Gine et al., "On-bead fluorescent DNA nanoprobes to analyze base excision repair Activities", Analytica Chimica Acta, vol. 812, 2014, pp. 168-175.
Hasatani et al.,"High-throughput and long-term observation of compartmentalized biochemical oscillators", Chem. Commun., 2013, vol. 49, pp. 8090-8092.
Hoke et al., "Effects of phosphorothioate capping on antisense oligonucleotide stability, hybridization and antiviral efficacy versus herpes simplex virus infection", Nucleic Acids Research, vol. 19, No. 20, pp. 5743-5748.
Holmberg et al., "The biotin-streptavidin interaction can be reversibly broken using water at elevated temperatures", Electrophoresis 2005, vol. 26, pp. 501-510.
Joos et al., "Covalent Attachment of Hybridizable Oligonucleotides to Glass Supports", Analytical Biochemistry 247, 96-101 (1997) Article No. AB972017.
Jung et al., "A stochastic DNA walker that traverses a microparticle surface", Nature Nanotechnology, vol. 11, Feb. 2016, pp. 157-164.
Kellar et al.,"Multiplexed Fluorescent Bead-Based Immunoassays for Quantitation of Human Cytokines in Serum and Culture Supernatants", Cytometry, vol. 45, pp. 27-36, 2001.
Kim et al., "Construction of an in vitro bistable circuit from synthetic transcriptional switches", Molecular Systems Biology, 2006, pp. 1-12.
Lambert et al., "cDNA library construction from small amounts of RNA using paramagnetic beads and PCR", Nucleic Acids Research, 1993, vol. 21, No. 3, pp. 775-776.
Mazutis et al., "Droplet-Based Microfluidic Systems for High-Throughput Single DNA Molecule Isothermal Amplification and Analysis", Anal. Chem. 2009, vol. 81, pp. 4813-4821.
Moina et al., "Nuclease Resistance and Antisense Activity of Modified Oligonucleotides Targeted to Ha-ras*", The Journal of Biological Chemistry, vol. 271, No. 24, Issue of Jun. 14, p. 14533-14540, 1996.
Montagne et al., "Programming an in vitro DNA oscillator using a molecular networking strategy", molecular systems biology, 2011, pp. 1-7.
Van Ness et al., "Isothermal reactions for the amplification of oligonucleotides", PNAS, Apr. 15, 2013, vol. 100, No. 8, pp. 4504-4509.
Padirac et al., "Bottom-up construction of in vitro switchable memories", PNAS, Oct. 29, 2012, E3212-E3220.
Padirac et al., "Nucleic acids for the rational design of reaction circuits", Current Opinion in Biotechnology, 2013, vol. 24, pp. 575-580.
Pandolfi et al., "Evaluation of Different Types of End-Capping Modifications on the Stability of Oligonucleotides Toward 3'- and 5'-Exonucleases", Nucleosides and Nucleotides, vol. 18, No. 9, pp. 2051-2069, 1999.
Qian et al., "Sequence dependence of isothermal DNA amplification via EXPAR", Nucleic Acids Research, 2012, vol. 40, No. 11, e87.
Rogers et al., "Immobilization of Oligonucleotides onto a Glass Support via Disulfide Bonds: A Method for Preparation of DNA Microarrays", Analytical Biochemistry 266, 23-30 (1999).
Rondelez et al., "Microfabricated arrays of femtoliter chambers allow single molecule enzymology", Nature Biotechnology, vol. 23, No. 3, Mar. 2005, pp. 361-365.
Schlingman et al., "A new method for the covalent attachment of DNA to a surface for single-molecule studies", Colloids Surf B Biointerfaces. Author manuscript; available in PMC Jan. 27, 2014.
Shukla et al., "Development of streptavidin-based nanocomplex for siRNA delivery", Mol Pharm. Dec. 2, 2013; 10(12): 4534-4545.
Taly et al., "Droplets as Microreactors for High-Throughput Biology", ChemBioChem 2007, 8, 263-272.
Tan et al., "Specific versus Nonspecific Isothermal DNA Amplification through Thermophilic Polymerase and Nicking Enzyme Activities", Biochemistry, 2008, vol. 47, pp. 9987-9999.
Thomson et al., "A custom microarray platform for analysis of microRNA gene expression", Nature Methods, vol. 1, No. 1, Oct. 2004, pp. 1-7.
Thomson et al., "Oligonucleotide and Polymer Functionalized Nanoparticles for Amplification-Free Detection of DNA", Biomacromolecules 2012, 13, 1981-1989.

(56) References Cited

OTHER PUBLICATIONS

Weitz et al., "Diversity in the dynamical behaviour of a compartmentalized programmable biochemical oscillator", Nature Chemisty, vol. 6, Apr. 2014.
Wittebolle et al., "Technical Note Optimisation of the amino-carboxy coupling of oligonucleotides to beads used in liquid arrays", Journal of Chemical Technology and Biotechnology, vol. 81, pp. 476-480, 2006.
Yamagata et al., "Overexpression, purification and characterization of RecJ protein from Thermus thermophiles HB8 and its core domain", Nucleic Acids Research, 2001, vol. 29, No. 22, pp. 4617-4624.
Yashin et al.," Networking Particles over Distance Using Oligonucleotide-Based Devices", J. Am. Chem. Soc. 2007, 129, 15581-15584.
Yuce et al., "Characterization of a dual biotin tag for improved single stranded DNA production", Anal. Methods, 2014, 6, pp. 548-557.
Zadorin et al., "Synthesis of Programmable Reaction-Diffusion Fronts Using DNA Catalyzers", PRL 114, 068301 (2015).
Zhang et al., "Lab on a single microbead: an ultrasensitive detection strategy enabling microRNA analysis at the single-molecule level", Chem. Sci., 2015, 6, 6213-6218.

* cited by examiner

FIG. 2

| ID | Sequence | |
|---|---|---|
| ODN1 | biotin AACTCGTCAGAATGCTCGTCAGAAT p | SEQ ID NO:1 |
| ODN2 | bioteg *C*A*A* TGA C5C CTG CAA TGA CTC CTG BMN5 | SEQ ID NO: 2 |
| ODN3 | bioteg*C*A*A*CGAC5CATCCAACGACTCATC FAM | SEQ ID NO: 3 |
| T1bioteg | bioteg *C*T*C*G*TCAGAATGCTCGTCAGAA p | SEQ ID NO: 4 |
| T1+Abioteg | bioteg *A*C*T*CGTCAGAATG CTCGTCAGAA p | SEQ ID NO: 5 |
| T1+AAbioteg | bioteg *A*A* C*TCGTCAGAATG CTCGTCAGAA p | SEQ ID NO: 6 |
| T1+Abiotin | biotin *A*C*T*CGTCAGAATGCTCGTCAGAA p | SEQ ID NO: 7 |
| T1+AAbiotin | biotin *A*A*C*TCGTCAGAATGCTCGTCAGAA p | SEQ ID NO: 8 |
| T1+AAAbiotin | biotin *A*A*A*CTCGTCAGAATGCTCGTCAGAA p | SEQ ID NO: 9 |
| αtoα | bioteg *C*T*C*G*TCAGAATGCTCGTCAGAAT p | SEQ ID NO: 10 |
| βtoβ | bioteg *C*G*A*TCCTGAATGCGATCCTGAAT p | SEQ ID NO: 11 |
| αtoβ | biotin AA CGA TCC TGA ATGCTCGTCAGAATG p | SEQ ID NO: 12 |
| pTα | biotin *A*A* AAAACTCGTCAGAATG p | SEQ ID NO: 13 |
| pTβ | biotin *A*A* AAAACGATCCTGAATG p | SEQ ID NO: 14 |
| α | CATTCTGACGAG | SEQID NO: 15 |
| β | CATTCAGGATCG | SEQ ID NO: 16 |
| Rβ | biotin TTTTG DDQII CATTCAATTTTCGATCCTGAATG Cy5 | SEQ ID NO: 17 |

| Enzymes | Concentration |
|---|---|
| ttRecJ exonuclease | 25 nM |
| Sequence | |
| ODN1 | 1 μM |
| Reaction buffer and temperature | |
| Tris-HCl, pH 7.9 | 20 nM |
| $(NH_4)_2SO_4$ | 10 mM |
| KCl | 10 mM |
| $MgSO_4$ | 8.4 mM |
| NaCl | 50 mM |
| Dithiothreiol | 3 mM |
| Synperonic F108 | 0.1 % |
| BSA | 200 μg/mL |
| Streptavidin | 0 or 1 μM |
| Evagreen | 1 X |
| Temperature | 45 °C |

Figure 5

| Enzymes | Concentration |
|---|---|
| Nb.BsmI nickase | 400 u/mL |
| Bst 2.0 warm start polymerase | 4 u/mL |
| ttRecJ exonuclease | 15 nM |
| Sequence | |
| T1xx | 100 nM |
| Reaction buffer and temperature | |
| Tris-HCl, pH 7.9 | 20 nM |
| $(NH_4)_2SO_4$ | 10 mM |
| KCl | 10 mM |
| $MgSO_4$ | 8.4 mM |
| NaCl | 50 mM |
| Dithiothreiol | 3 mM |
| Synperonic F108 | 0.1 % |
| BSA | 800 µg/mL |
| Streptavidin | 100 nM |
| Evagreen | 0.4 X |
| dATP, dCTP, dGTP, TTP | 50 µM |
| Temperature | 45 °C |

Figure 7

| Particles | |
| --- | --- |
| Part. A | ODN2 (BMN5) |
| Part. B | ODN3 (FAM) |
| Buffer and temperature | |
| Tris-HCl, pH 7.0 | 10 nM |
| MgSO$_4$ | 2 mM |
| NaCl | 100 mM |
| Temperature | 45 °C |

Figure 9

| Enzymes | Concentration |
| --- | --- |
| Nb.BsmI nickase | 400 u/mL |
| Bst 2.0 warm start polymerase | 4 u/mL |
| ttRecJ exonuclease | 25 nM |
| USER™ enzyme | 3 u/mL |

CompuSpheres $\alpha_M$

| | |
| --- | --- |
| Autocatalytic template | α to α (1nmol/mg part.) |
| Concentration | $4 \cdot 10^4$ part/mL |

Reaction buffer and temperature

| | |
| --- | --- |
| Tris-HCL, pH 7.9 | 20 nM |
| (NH4)2SO4 | 10 mM |
| KCl | 10 mM |
| MgSO4 | 8.4 mM |
| NaCl | 50 mM |
| Dithiothreiol | 3 mM |
| Synperonic F108 | 0.1 % |
| BSA | 800 µg/mL |
| Evagreen | 0.8X |
| dATP, dCTP, dGTP, TTP | 25 µM |
| dUTP | 2.5 µM |
| Temperature | 45 °C |

Figure 11

| Enzymes | Concentration |
|---|---|
| Nb.BsmI nickase | 400 u/mL |
| Bst 2.0 warm start polymerase | 4 u/mL |
| ttRecJ exonuclease | 10 nM |
| USER™ enzyme | 3 u/mL |
| CompuSpheres $\alpha_M$ | |
| Autocatalytic template | $\alpha$ to $\alpha$ (1nmol/mg part.) |
| Amount | 1 |
| Reaction buffer and temperature | |
| Tris-HCL, pH 7.9 | 20 nM |
| (NH4)2SO4 | 10 mM |
| KCl | 10 mM |
| MgSO4 | 8.4 mM |
| NaCl | 50 mM |
| Dithiothreiol | 3 mM |
| Synperonic F108 | 0.1 % |
| BSA | 800 µg/mL |
| Evagreen | 0.4 X |
| dATP, dCTP, dGTP, TTP | 50 µM |
| dUTP | 5 µM |
| Temperature | 45 °C |

Figure 13

| Enzymes | Concentration |
|---|---|
| Nb.BsmI nickase | 400 u/mL |
| Bst 2.0 warm start polymerase | 4 u/mL |
| ttRecJ exonuclease | 10 nM |
| USER™ enzyme | 3 u/mL |
| CompuSpheres $\alpha_B$ | |
| Autocatalytic template | $\alpha$to$\alpha$ (1 nmol/mg part.) |
| Pseudo-template | pT$\alpha$ ( 0.3 nmol/mg part.) |
| Concentration | $4 \cdot 10^4$ part/mL |
| Reaction buffer and temperature | |
| Tris-HCL, pH 7.9 | 20 nM |
| $(NH_4)_2SO_4$ | 10 mM |
| KCl | 10 mM |
| $MgSO_4$ | 8.4 mM |
| NaCl | 50 mM |
| Dithiothreiol | 3 mM |
| Synperonic F108 | 0.1 % |
| BSA | 800 µg/mL |
| Evagreen | 0.4 X |
| dATP, dCTP, dGTP, TTP | 50 µM |
| dUTP | 5 µM |
| Temperature | 45 °C |

Figure 15

| Enzymes | |
|---|---|
| Nb.BsmI nickase | 400 u/mL |
| Bst 2.0 warm start polymerase | 2.8 u/mL |
| ttRecJ exonuclease | 25 nM |
| USER™ enzyme | 3 u/mL |
| CompuSpheres $\alpha_B$ | |
| Autocatalytic template | αtoα (1 nmol/mg part.) |
| Pseudo-template | pTα (0.4 nmol/mg part.) |
| Concentration | $8 \cdot 10^4$ part/mL |
| CompuSpheres $\beta_B$ | |
| Autocatalytic template | βtoβ (1 nmol/mg part.) |
| Pseudo-template | pTβ (0.3 nmol/mg part.) |
| Concentration | $8 \cdot 10^4$ part/mL |
| Reaction buffer and temperature | |
| Tris-HCL, pH 7.9 | 20 nM |
| (NH4)2SO4 | 10 mM |
| KCl | 10 mM |
| MgSO4 | 8.4 mM |
| NaCl | 50 mM |
| Dithiothreiol | 3 mM |
| Synperonic F108 | 0.1 % |
| BSA | 800 µg/mL |
| Evagreen | 0.4 X |
| dATP, dCTP, dGTP, TTP | 50 µM |
| dUTP | 5 µM |
| Temperature | 45 °C |

Figure 17

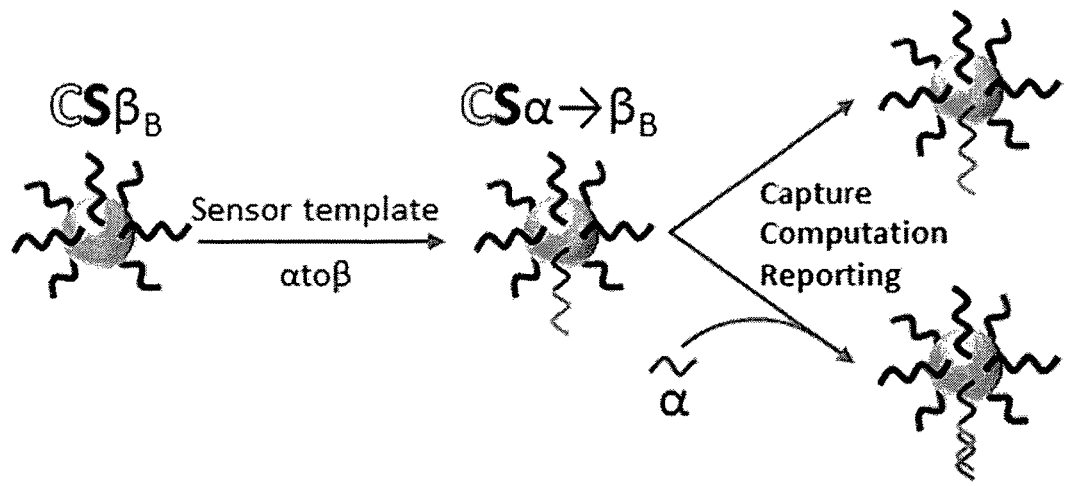
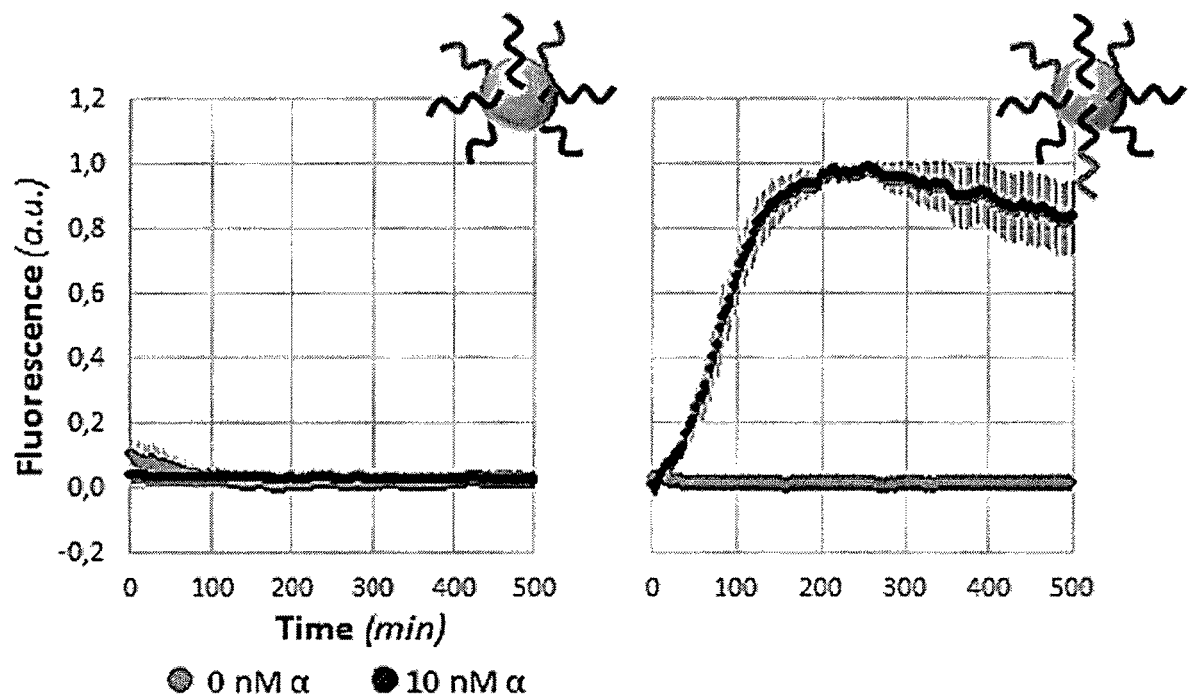
Figure 18

| Enzymes | |
|---|---|
| Nb.BsmI nickase | 400 u/mL |
| Bst 2.0 warm start polymerase | 2.8 u/mL |
| ttRecJ exonuclease | 25 nM |
| USER™ enzyme | 3 u/mL |
| CompuSpheres $\alpha \rightarrow \beta_B$ | |
| Autocatalytic template | $\beta to \beta$ (1 nmol/mg part.) |
| Pseudo-template | $pT\beta$ (0.3 nmol/mg part.) |
| Sensor template | $\alpha to \beta$ (0.1 nmol/mg part.) |
| Concentration | $8 \cdot 10^4$ part/mL |
| Reaction buffer and temperature | |
| Tris-HCl, pH 7.9 | 20 nM |
| $(NH_4)_2SO_4$ | 10 mM |
| KCl | 10 mM |
| $MgSO_4$ | 8.4 mM |
| NaCl | 50 mM |
| Dithiothreiol | 3 mM |
| Synperonic F108 | 0.1 % |
| BSA | 800 µg/mL |
| Evagreen | 0.4 X |
| dATP, dCTP, dGTP, TTP | 100 µM |
| dUTP | 10 µM |
| Temperature | 45 °C |

Figure 19

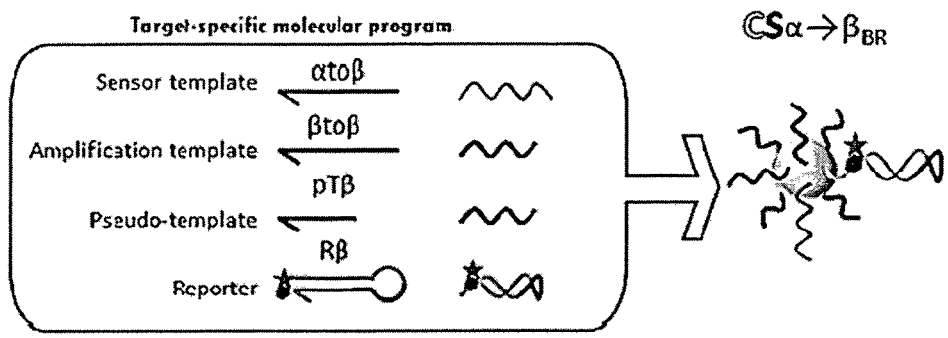
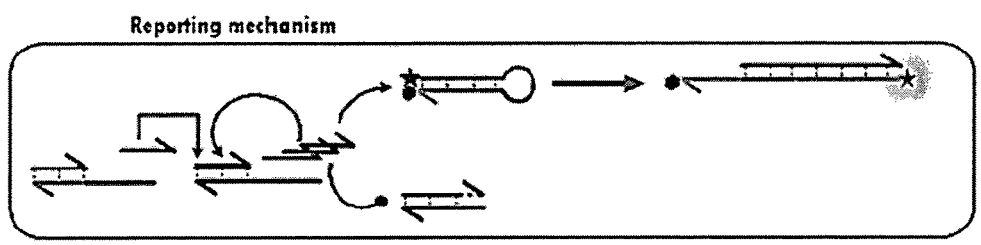
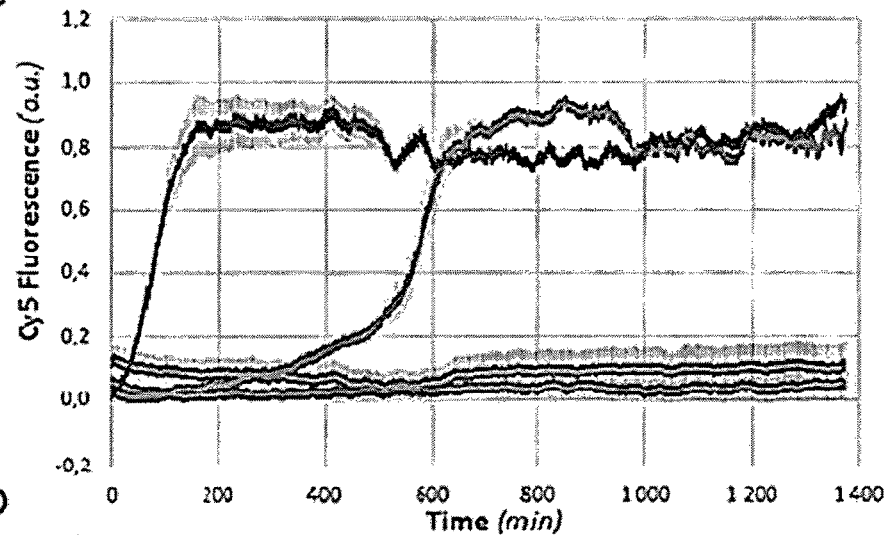
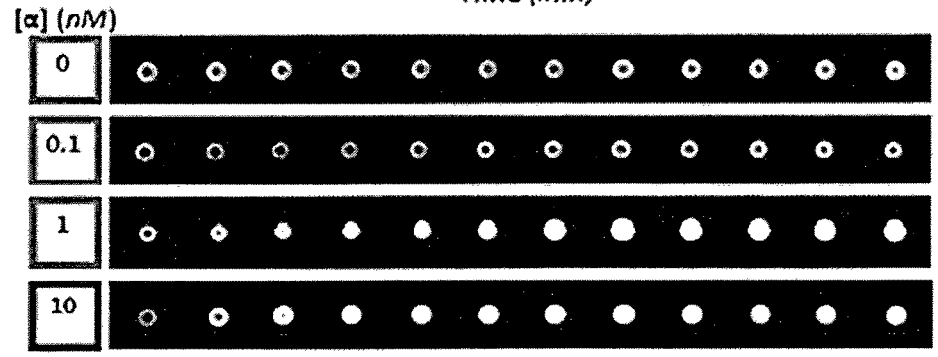
Figure 20

| Enzymes | |
|---|---|
| Nb.BsmI nickase | 400 u/mL |
| Bst 2.0 warm start polymerase | 2.8 u/mL |
| USER™ enzyme | 3 u/mL |
| CompuSpheres α→β$_{BR}$ | |
| Autocatalytic template | βtoβ (1 nmol/mg part.) |
| Pseudo-template | pTβ (0.3 nmol/mg part.) |
| Sensor template | αtoβ (0.1 nmol/mg part.) |
| Reporter | Rβ (0.7 nmol/mg part.) |
| Concentration | 8 10$^4$ part/mL |
| Reaction buffer and temperature | |
| Tris-HCl, pH 7.9 | 20 nM |
| (NH$_4$)$_2$SO$_4$ | 10 mM |
| KCl | 10 mM |
| MgSO$_4$ | 8.4 mM |
| NaCl | 50 mM |
| Dithiothreiol | 3 mM |
| Synperonic F108 | 0.1 % |
| BSA | 800 µg/mL |
| Evagreen | 0.4 X |
| dATP, dCTP, dGTP, TTP | 100 µM |
| dUTP | 10 µM |
| Temperature | 45 °C |

Figure 21

MOLECULAR COMPUTING COMPONENT AND METHOD OF MOLECULAR COMPUTING

CROSS-REFERENCE TO RELATED APPLICATIONS

This application is the National Phase of International Patent Application No. PCT/IB2016/000419, filed Feb. 16, 2016, published on Aug. 24, 2017 as WO/2017/141068 A1. The contents of this application is herein incorporated by reference in its entirety.

SEQUENCE LISTING

The instant application contains a Sequence Listing which has been submitted in ASCII format via EFS-WEB and is hereby incorporated by reference in its entirety. Said ASCII copy, created on Nov. 24, 2020, is named 065691-3800_Sequence.txt and is 4,096 bytes in size.

TECHNICAL FIELD

The present invention relates to a molecular computing component and a method of molecular computing.

BACKGROUND ART

Hitherto, molecular programming has become a growing field that attempts to create new information-processing systems using molecules: DNA strands as information careers and chemical reactions as processing elements. This technique has led to the developments of various biomolecules-based circuit-building approaches (using for example DNA, RNA, proteins and enzymes). In this context, Polymerase/Exonuclease/Nickase Dynamic Network Assembly (PEN-DNA) toolbox was developed (see, for example, NPL 1 and 2).

The PEN-DNA toolbox uses a 3-enzyme machinery (polymerase, exonuclease, nickase) to drive the fabrication, exchange and degradation of signal-carrying DNA strands: a DNA-polymerase elongates a short input strand that hybridizes on the input 3' side of a matching DNA template (a single-stranded oligonucleotide of a few tens of bases long); a nickase site-specifically nicks the resulting full duplex, releasing both the input and a new single strand DNA output complementary to the output side of the template. The exonuclease (usually of the RecJ family, but it can be another exonuclease) unspecifically degrades all unprotected single-stranded oligonucleotides but not templates or reporter strands, which are protected using DNA modifications or substitutions, maintaining the system in a responsive out-of-equilibrium state. The PEN-DNA toolbox, as a solution-phase biomolecular reaction networking scheme, has allowed the construction of various dynamic circuits such as multistable, oscillatory and excitable systems (see, for example, NPL 3-5). For example, a molecular program can be used to create a bistable molecular mixture. As long as fuel is available, such a system will stay in one of two possible dynamic steady-states unless a perturbation is applied to switch it to the alternative state, where it will again settle, thus keeping the memory of the applied perturbation. These states are called "dynamic steady states" because they are not at thermodynamic equilibrium, but correspond to constant equilibrated production and degradation of circuit compounds (here short DNA strands) so that all these concentrations are stationary (but in a close system, fuel concentration will decrease and waste concentration will increase). Such bistable systems can be used to detect some molecular targets, without being affected by molecular noise or background reactions, because the switching threshold is set to be above such noise or background. As such, molecular systems programmed to display bistability have an important potential for the selective detection of molecular targets.

CITATION LIST

Non Patent Literature

[NPL 1]
Montagne K, Plasson R, Sakai Y, Fujii T, Rondelez Y. Programming an in vitro DNA oscillator using a molecular networking strategy. Mol Syst Biol. 2011 Feb. 1; 7:466.

[NPL 2]
Baccouche A, Montagne K, Padirac A, Fujii T, Rondelez Y. Dynamic DNA-toolbox reaction circuits: A walkthrough. Methods. 2014 May 15; 67(2):234-49.

[NPL 3]
Padirac A, Fujii T, Rondelez Y. Bottom-up construction of in vitro switchable memories. Proc Natl Acad Sci. 2012 Nov. 20; 109(47):E3212-20.

[NPL 4]
Padirac A, Fujii T, Rondelez Y. Nucleic acids for the rational design of reaction circuits. Curr Opin Biotechnol. 2013 August; 24(4):575-80.

[NPL 5]
Fujii T, Rondelez Y. Predator-Prey Molecular Ecosystems. ACS Nano. 2013 Jan. 22; 7(1):27-34.

[NPL 6]
Zadorin A S, Rondelez Y, Galas J-C, Estevez-Torres A. Synthesis of Programmable Reaction-Diffusion Fronts Using DNA Catalyzers. Phys Rev Lett. 2015 Feb. 9; 114(6):068301.

[NPL 7]
Chou J, Wong J, Christodoulides N, Floriano P N, Sanchez X, McDevitt J. Porous Bead-Based Diagnostic Platforms: Bridging the Gaps in Healthcare. Sensors. 2012 Nov. 9; 12(11):15467-99.

[NPL 8]
Wang Y, Shi J, Wu Y, Xu W, Wang Q, Zhang J, et al. Use of Luminex xMAP bead-based suspension array for detecting microRNA in NSCLC tissues and its clinical application. Tumori. 2012 November; 98(6):792-9.

[NPL 9]
Bartosik M, Hrstka R, Palecek E, Vojtesek B. Magnetic bead-based hybridization assay for electrochemical detection of microRNA. Anal Chim Acta. 2014 Feb. 27; 813:35-40.

[NPL 10]
Ferguson J A, Steemers F J, Walt D R. High-Density Fiber-Optic DNA Random Microsphere Array. Anal Chem. 2000 Nov. 1; 72(22):5618-24.

[NPL 11]
Gines G, Saint-Pierre C, Gasparutto D. A multiplex assay based on encoded microbeads conjugated to DNA Nano-Beacons to monitor base excision repair activities by flow cytometry. Biosens Bioelectron. 2014 Aug. 15; 58:81-4.

[NPL 12]
Kellar K L, Kalwar R R, Dubois K A, Crouse D, Chafin W D, Kane B-E. Multiplexed fluorescent bead-based immu-

[NPL 12]

noassays for quantitation of human cytokines in serum and culture supernatants. Cytometry. 2001 Sep. 1; 45(1): 27-36.

[NPL 13]
Joos B, Kuster H, Cone R. Covalent Attachment of Hybridizable Oligonucleotides to Glass Supports. Anal Biochem. 1997 Apr. 5; 247(1):96-101.

[NPL 14]
Wittebolle L, Verstuyft K, Verstraete W, Boon N. Optimisation of the amino-carboxy coupling of oligonucleotides to beads used in liquid arrays. J Chem Technol Biotechnol. 2006 Mar. 1; 81(3):476-80.

[NPL 15]
Schlingman D J, Mack A H, Mochrie S G J, Regan L. A new method for the covalent attachment of DNA to a surface for single-molecule studies. Colloids Surf B Biointerfaces. 2011 March; 83(1):91-5.

[NPL 16]
Rogers Y H, Jiang-Baucom P, Huang Z J, Bogdanov V, Anderson S, Boyce-Jacino M T. Immobilization of oligonucleotides onto a glass support via disulfide bonds: A method for preparation of DNA microarrays. Anal Biochem. 1999 Jan. 1; 266(1):23-30.

[NPL 17]
Chrisey L A, Lee G U, O'Ferrall C E. Covalent attachment of synthetic DNA to self-assembled monolayer films. Nucleic Acids Res. 1996 Aug. 1; 24(15):3031-9.

[NPL 18]
Adessi C, Matton G, Ayala G, Turcatti G, Mermod J-J, Mayer P, et al. Solid phase DNA amplification: characterisation of primer attachment and amplification mechanisms. Nucleic Acids Res. 2000 Oct. 15; 28(20):e87-e87.

[NPL 19]
Thomson D A C, Tee E H L, Tran N T D, Monteiro M J, Cooper M A. Oligonucleotide and Polymer Functionalized Nanoparticles for Amplification-Free Detection of DNA. Biomacromolecules. 2012 Jun. 11; 13(6):1981-9.

[NPL 20]
Yuce M, Kurt H, Budak H. Characterization of a dual biotin tag for improved single stranded DNA production. Anal Methods. 2013 Dec. 19; 6(2):548-57.

[NPL 21]
Lambert K N, Williamson V M. cDNA library construction from small amounts of RNA using paramagnetic beads and PCR. Nucleic Acids Res. 1993 Feb. 11; 21(3):775-6.

[NPL 22]
Fan Z H, Mangru S, Granzow R, Heaney P, Ho W, Dong Q, et al. Dynamic DNA Hybridization on a Chip Using Paramagnetic Beads. Anal Chem. 1999 Nov. 1; 71(21): 4851-9.

[NPL 23]
Dressman D, Yan H, Traverso G, Kinzler K W, Vogelstein B. Transforming single DNA molecules into fluorescent magnetic particles for detection and enumeration of genetic variations. Proc Natl Acad Sci. 2003 Jul. 22; 100(15):8817-22.

[NPL 24]
Ayukawa S, Takinoue M, Kiga D. RTRACS: A Modularized RNA-Dependent RNA Transcription System with High Programmability. Acc Chem Res. 2011 Dec. 20; 44(12): 1369-79.

[NPL 25]
Kim J, White K S, Winfree E. Construction of an in vitro bistable circuit from synthetic transcriptional switches. Mol Syst Biol. 2006; 2:68.

[NPL 26]
Yamagata A, Masui R, Kakuta Y, Kuramitsu S, Fukuyama K. Overexpression, purification and characterization of RecJ protein from *Thermus thermophilus* HB8 and its core domain. Nucleic Acids Res. 2001 Nov. 15; 29(22):4617-24.

[NPL 27]
Hoke G D, Draper K, Freier S M, Gonzalez C, Driver V B, Zounes M C, et al. Effects of phosphorothioate capping on antivense oligonucleotide stability, hybridization and antiviral efficacy versus herpes simplex virus infection. Nucleic Acids Res. 1991 Oct. 25; 19(20):5743-8.

[NPL 28]
Behlke M A. Chemical modification of siRNAs for in vivo use. Oligonucleotides. 2008 Dec.; 18(4):305-19.

[NPL 29]
Pandolfi D, Rauzi F, Capobianco M L. Evaluation of different types of end-capping modifications on the stability of oligonucleotides toward 3'- and 5'-exonucleases. Nucleosides Nucleotides. 1999 September; 18(9):2051-69.

[NPL 30]
Monia B P, Johnston J F, Sasmor H, Cummins L L. Nuclease resistance and antisense activity of modified oligonucleotides targeted to Ha-ras. J Biol Chem. 1996 Jun. 14; 271(24):14533-40.

[NPL 31]
Barawkar D A, Bruice T C. Synthesis, biophysical properties, and nuclease resistance properties of mixed backbone oligodeoxynucleotides containing cationic internucleoside guanidinium linkages: Deoxynucleic guanidine/DNA chimeras. Proc Natl Acad Sci USA. 1998 Sep. 15; 95(19):11047-52.

[NPL 32]
Dias N, Stein C A. Antisense Oligonucleotides: Basic Concepts and Mechanisms. Mol Cancer Ther. 2002 Mar. 1; 1(5):347-55.

[NPL 33]
Boado R J, Pardridge W M. Complete protection of antisense oligonucleotides against serum nuclease degradation by an avidin-biotin system. Bioconjug Chem. 1992 Nov. 1; 3(6):519-23.

[NPL 34]
Shukla R S, Tai W, Mahato R, Jin W, Cheng K. Development of streptavidin-based nanocomplex for siRNA delivery. Mol Pharm. 2013 Dec. 2; 10(12):4534-45.

[NPL 35]
Gines G, Saint-Pierre C, Gasparutto D. On-bead fluorescent DNA nanoprobes to analyze base excision repair activities. Anal Chim Acta. 2014 Feb. 17; 812:168-75.

[NPL 36]
Holmberg A, Blomstergren A, Nord O, Lukacs M, Lundeberg J, Uhlen M. The biotin-streptavidin interaction can be reversibly broken using water at elevated temperatures. Electrophoresis. 2005 February; 26(3):501-10.

[NPL 37]
K F, J S. Surprising lability of biotin-streptavidin bond during transcription of biotinylated DNA bound to paramagnetic streptavidin beads. BioTechniques. 1993 April; 14(4):608-17.

[NPL 38]
Cradic K W, Wells J E, Allen L, Kruckeberg K E, Singh R J, Grebe S K G. Substitution of 3'-Phosphate Cap with a Carbon-Based Blocker Reduces the Possibility of Fluorescence Resonance Energy Transfer Probe Failure in Real-Time PCR Assays. Clin Chem. 2004 Jun. 1; 50(6): 1080-2.

[NPL 39]
Xia Q-F, Xu S-X, Wang D-S, Wen Y-A, Qin X, Qian S-Y, et al. Development of a novel quantitative real-time assay using duplex scorpion primer for detection of *Chlamydia trachomatis*. Exp Mol Pathol. 2007 August; 83(1):119-24.

[NPL 40]
Ness J V, Ness L K V, Galas D J. Isothermal reactions for the amplification of oligonucleotides. Proc Natl Acad Sci. 2003 Apr. 15; 100(8):4504-9.

[NPL 41]
Zhang X, Liu C, Sun L, Duan X, Li Z. Lab on a single microbead: an ultrasensitive detection strategy enabling microRNA analysis at the single-molecule level. Chem Sci [Internet]. 2015 Aug. 20 [cited 2015 Aug. 28]; Available from: http://pubs.rsc.org/en/content/articlelanding/2015/sc/c5sc02641e

[NPL 42]
Qian J, Ferguson T M, Shinde D N, Ramirez-Borrero A J, Hintze A, Adami C, et al. Sequence dependence of isothermal DNA amplification via EXPAR. Nucleic Acids Res. 2012 June; 40(11):e87.

[NPL 43]
Tan E, Erwin B, Dames S, Ferguson T, Buechel M, Irvine B, et al. Specific versus Nonspecific Isothermal DNA Amplification through Thermophilic Polymerase and Nicking Enzyme Activitiest. Biochemistry (Mosc). 2008 Sep. 23; 47(38):9987-99.

[NPL 44]
Weitz M, Kim J, Kapsner K, Winfree E, Franco E, Simmel F C. Diversity in the dynamical behaviour of a compartmentalized programmable biochemical oscillator. Nat Chem. 2014 April; 6(4):295-302.

[NPL 45]
Hasatani K, Leocmach M, Genot A J, Estevez-Ibrres A, Fujii T, Rondelez Y. High-throughput and long-term observation of compartmentalized biochemical oscillators. Chem Commun Camb Engl. 2013 Sep. 21; 49(73):8090-2.

[NPL 46]
Taly V, Kelly B T, Griffiths A D. Droplets as microreactors for high-throughput biology. Chembiochem Eur J Chem Biol. 2007 Feb. 12; 8(3):263-72.

[NPL 47]
Mazutis L, Araghi A F, Miller O J, Baret J-C, Frenz L, Janoshazi A, et al. Droplet-Based Microfluidic Systems for High-Throughput Single DNA Molecule Isothermal Amplification and Analysis. Anal Chem. 2009 Jun. 15; 81(12):4813-21.

[NPL 48]
Rondelez Y, Tresset G, Tabata K V, Arata H, Fujita H, Takeuchi S, et al. Microfabricated arrays of femtoliter chambers allow single molecule enzymology. Nat Biotechnol. 2005 March; 23(3):361-5.

[NPL 49]
Thomson J M, Parker J, Perou C M, Hammond S M. A custom microarray platform for analysis of microRNA gene expression. Nat Methods. 2004 October; 1(1):47-53.

[NPL 50]
Yashin R, Rudchenko S, Stojanovic M N. Networking Particles over Distance Using Oligonucleotide-Based Devices. J Am Chem Soc. 2007 Dec. 1; 129(50):15581-4.

[NPL 51]
Jung C, Allen P B, Ellington A D. A stochastic DNA walker that traverses a microparticle surface. Nat Nanotechnol [Internet]. 2015 Nov. 2 [cited 2016 Jan. 15]; advance online publication.

SUMMARY OF INVENTION

Technical Problem

However, in the aforementioned PEN-DNA toolbox, the computation is performed in an amorphous aqueous solution (typically in a test tube) that limits multiplexing capabilities because it is difficult to have multiple independent programs running simultaneously in the same sample. This is because multiple circuits would need to share the enzymatic machinery and may interact in an undesired way (NPL 2, 5, 6), for example, by spurious binding of DNA strands that are not expected to interact in the designed circuit. Alternatively each circuit should be prepared in a different test tube, so if one wants to perform different tasks, this involves complex manipulations and multiple pipetting of many components to prepare each test tube, increasing the risk of experimental errors. Moreover, because the volume of an individual experiment is a few microliters, the total consumption of expensive reagents such as enzymes or synthetic oligonucleotides can be important. Altogether, these reasons limit the application of programmed molecular circuits for biosensing or diagnostics applications.

An object of the present invention is to provide a molecular computing component and a method of molecular computing that can be applied to detect rare molecular targets while filtering out background noise and avoiding unspecific signal generation and false positives but is also miniaturized, easy to use for the end user, and allows parallel operations in one single tube.

Solution to Problem

Accordingly, the present description provides a component for detection of molecular targets, the component comprising: a microsphere including pores, at least some of which are open on a surface of the microsphere, and a plurality of modules attached to the microsphere wherein each of the modules is a continuous sequence of nucleic acid bases, and multiple copies of each of the modules are linked to the microsphere.

In another component, the modules grafted on the microsphere locally cooperate to evaluate chemical signals in their environment, compute a response and generate a reporting signal if appropriate.

In yet another component, the component comprises a plurality of the microspheres, and the microspheres concurrently exist in an identical sample.

In yet another component, the microspheres are of different types, and each of the microspheres has a distinct combination of modules, thereby each of the microspheres performs a different function.

In yet another component, the different types of microspheres can be distinguished by the combination of fluorescent barcodes grafted thereon at the same time of synthesis.

In yet another component, a molecular circuit with sensing function is encoded by a combination of the modules attached to the microsphere, the modules cooperate essentially locally on the microsphere through exchanges of short DNA strands and the exchanges define a function of the component.

In yet another component, the component comprises a plurality of the microspheres, each of the microspheres performs its function independently in an identical solution.

The present description also provides a method of molecular computing with a component comprising a plurality of microspheres including pores, at least some of which are open on a surface of the microspheres, and a plurality of modules grafted on the microspheres wherein each of the modules is a DNA strand, the method comprising steps of designing the modules and their combinations to create one or more molecular programs; attaching each molecular program to a batch of the microspheres; bringing a set of these grafted microspheres, each of which carries its own molecular program, into contact with a solution containing one or more target compounds and a mixture of enzymes; and incubating the grafted microspheres with the mixture of enzymes at a constant temperature so that DNA production and exchange happen locally on each microsphere in between the grafted modules according to a specific molecular program of the microsphere.

In another method, the mixture of enzymes contains one or more of such activities as polymerase, nickase and exonuclease.

In yet another method, the modules include a first and second template, the first template is an amplification template, the second template absorbs leak reaction and avoids unspecific spontaneous amplification when the microsphere contacts with the mixture of enzymes, so that DNA is amplified exponentially only when the first template receives stimulation above a predetermined concentration threshold for a specific target specie.

In yet another method, the modules include a third template, the third template is a target-conversion template, the target-conversion template is able to capture a target nucleic acid strand and consequently stimulate the first template so that the threshold is crossed, amplification happens, and existence of the target strand is sensed.

In yet another method, the modules include a fourth template, the fourth template is a reporter strand, the reporter strand generates a fluorescence signal using a product of the amplification template so that existence of the target strand is reported.

Advantageous Effects of Invention

According to the current disclosure, the molecular computing component is programmable, modular, miniaturized, autonomous, reusable, active and has multiplexing capabilities.

BRIEF DESCRIPTION OF DRAWINGS

FIG. 2 is a table of sequences used throughout the present embodiment.
FIG. 5 is a first table showing experimental condition in Example 1 (FIG. 4).
FIG. 7 is a second table showing experimental condition in Example 1 (FIG. 6).
FIG. 9 is a third table showing experimental condition in Example 1 (FIG. 8).
FIG. 11 is a first table showing experimental condition in Example 2 (FIG. 10).
FIG. 13 is a second table showing experimental condition in Example 2 (FIG. 12).
FIG. 15 is a table showing experimental condition in Example 3.
FIG. 17 is a table showing experimental condition in Example 4.
FIG. 18 is a set of schematic views of CompuSpheres embedding a bistable system (amplification+leak-absorbing template modules) and a target-conversion module.
FIG. 19 is a table showing experimental condition in Example 5.
FIG. 20 is a set of schematic views showing experimental results of target detection with CompuSpheres grafted with a specific reporter strand.
FIG. 21 is a table showing experimental condition in Example 6.

DESCRIPTION OF EMBODIMENTS

An embodiment will be described in detail with reference to the drawings.

Figure 1:
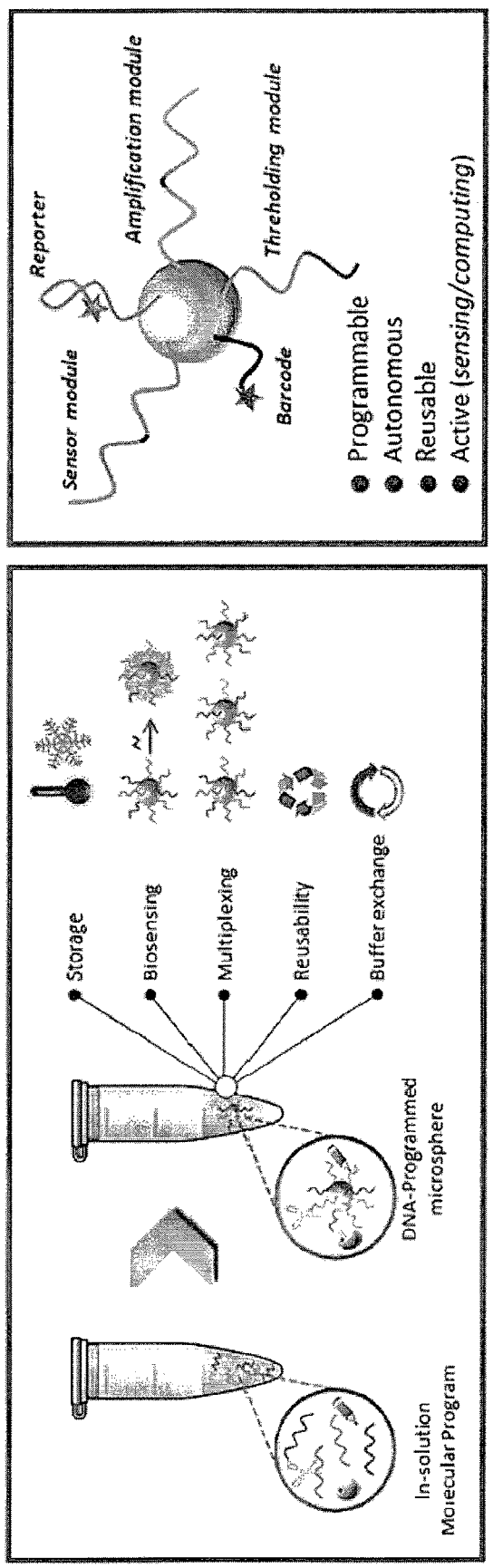
FIG. 1 is a set of schematic views of CompuSpheres.

FIG. 1 is a set of schematic views of CompuSpheres. FIG. 2 is a table of sequences used throughout the present embodiment.

The respective figures disclose an embodiment involving fabrication of autonomous programmed particles by grafting all DNA encoding components of a PEN-DNA molecular program within porous microspheres. As shown in FIG. 1, it is possible to synthesize in parallel millions of microspheres implanted with identical or different programs. The novelty of these microspheres (compared to other beads or particle-based molecular protocols used in molecular biology or diagnostics (NPL 7-9)) lies in the pre-encoded information-processing capability of the particle, which comes from its decoration by the grafting of the rule-encoding DNA templates of the PEN DNA toolbox. Implementation of this molecular program will start as soon as the particle is contacted with the required set of enzymatic activities, fuel molecules and molecular inputs, through the production and exchange of short DNA single strands, mostly within the porous material of a single bead. While some produced oligonucleotides can diffuse away, local behavior is dominant because of the high local concentration of grafted oligonucleotides, the dilution and degradation of those signals as they diffuse away from the microsphere, and react with enzymes such as exonuclease. Therefore, the molecular program now runs locally, instead of being distributed over a solution, and multiple, possibly different programs can run on different beads in the same solution. As a result it is demonstrated that programmed microspheres are able to sense, compute and report autonomously according to their environment (for instance, detect the presence or absence of a target strand), and that this happens locally and in a parallel fashion. This DNA-programmed microspheres are called CompuSphere (CS), for more simplicity in this description. Note that a number of companies offers microbead-based assay (polystyrene, glass-made, magnetic, etc.) for biomedical applications. These beads are typically functionalized with a specific probe (antibody, nucleic acid strand) and their exposure to the sample containing the target (protein, analytes, DNA or RNA sequence, etc.) results in binding of the target, followed by an optical or electrochemical readout. For references, see patent WO 2006125124A2 or NPL 7-9. These assays are then different from the present disclosure, where the beads carry a complex molecular program involving multiple strands of DNA and designed to provide an improved sensing function.

FIG. 1 shows a schematic representation of CompuSphere. DNA-based molecular programs are transposed from the solution-phase format to particle-supported format by grafting a set of encoding modules on porous microspheres. The resulting DNA-programmed particles are suitable for biosensing applications thanks to easy storage, buffer exchange, and high multiplexing capabilities. In comparison with other particles whose outer surfaces are decorated with DNA, used in various biotechnological applications. CompuSphere more specifically refers to porous particles that localize an information-processing molecular program in their bulk, thanks to a co-grafting of different modules (including for example one or more target-conversion module, one or more amplification module, one or more thresholding module, one or more reporter module and one or more barcode module, as defined below).

Because CompuSpheres can be prepared in advance with a defined mixture of encoding modules and barcodes, their usage is very simple to end-users, who just need to place them in contact with a liquid solution and incubate at constant temperature to start operations (or possibly perform a sequence of contact/exchange steps with various solutions). The present embodiment therefore proposes the packaging of one or multiple multicomponent molecular program onto easy-to-handle particles and brings the possibility of highly parallel, information-processing operations with limited use of reagents. It is expected to bring a major breakthrough in the usage of complex molecular protocols, and in particular to impact miniaturized, multiplexed, smart molecular diagnostics approaches (biosensing).

In the present embodiment, an experimental procedure starts by functionalizing mesoporous particles with a defined mixture of DNA modules (oligonucleotides that act as rules of the molecular program, and can be for example target-conversion template, amplification template, thresholding template, reporter probe, etc. and are modified for surface binding) and a fluorescent barcode element. After this synthesis step, the CompuSphere are washed and can be stored for several months at 4° C. or possibly dried and kept at room temperature. An application of these CompuSphere will typically consist in exposing them to the sample containing one or more targets (the biomolecular of interest, for example, DNA or RNA sequences), adding a mixture of enzyme, and incubating at constant temperature. Each CompuSphere will compute a response depending on the presence/absence and concentration of their specific target in the sample, and the result will materialize as amplification of DNA, which can be detected by looking at the fluorescent barcode and reporter signals of each CompuSphere. In the following description biotin-avidin linkage is used to attach the oligonucleotides to the porous microsphere, but many other grafting chemistry could be used to attach the DNA instructions to the porous microspheres including but not limited to amino coupling (NPL 13-15), disulfide bonds (NPL 16), self-assembled monolayer (NPL 17), other thiol-reactive chemistry (NPL 18), click chemistry (NPL 19), dual-biotin-avidin linkage (NPL 20), nucleic linker-mediated hybridization (NPL 21) and any covalent ligation and non-covalent immobilization chemistry.

It will be demonstrated that CompuSpheres are:

Programmable; for example each independent particle is designed to compute the presence/absence of a specific DNA or RNA target above a user-defined threshold Autonomous; they do this task on their own and sustain the amplified state corresponding to a positive detection as long as fuel dNTPs and catalytic activities are provided Reusable; they go back to the initial state if fuel is removed, if catalytic activities are removed or if they are washed Environment sensitive; they can sense molecules present in the surrounding solution (they are not physically compartmentalized as in many other high-throughput strategies).

Modular; each module can be designed and attached independently or jointly on the microspheres making the programming of microspheres versatile.

Multiplexable (able of multiplex operation): particles carrying different molecular programs can perform different sensing operations in the same solution.

Through next six Examples, the following (a)-(f) will be shown.

(a) The programming of microspheres with DNA modules requires some adjustments with respect to well-mixed molecular programing protocols (where rule-encoding templates are not attached to a solid phase, but free in solution).

In particular, compared to the PEN DNA toolbox, the design rules of the encoding template's sequences does not change, but one needs to add appropriate spacers and linkers. Given these adjustments, the qualitative dynamic behavior, and hence the molecular programming rules, are basically the same on the particles as they are in the solution.

(b) CompuSpheres exhibit autonomous computational capabilities, applicable for example to the detection of nucleic acid targets.

(c) CompuSpheres are suitable for multiplex assay. Different CompuSpheres in the same solution can perform different tasks and results can be extracted using fluorescent reporters and barcodes.

(d) A versatile assay can be designed by coupling a bistable amplification motif (the same for all targets) and target-conversion modules (specifically designed for each target of interest), using simple design rules.

(e) Unspecific reporters such as SybrGreen or EvaGreen provide a straightforward way to monitor the results of CompuSphere based protocols. Alternatively, a specific reporter strategy can be designed to provide higher signal, higher detection specificity or to multiplex assays.

(f) One CompuSphere can integrate a variety of decorating templates cooperating to provide an integrated function. For example, one CompuSphere can carry an amplification module, a leak-absorption module, a target-conversion module, a specific reporter strand and a spectrally orthogonal fluorescent barcode.

In the tables and following text, biotin and bioteg refer to biotinylated synthons, respectively using aminoethoxyethoxyethanol linker and the longer triethylene glycol linker. "*" denotes a phosphorothioate backbone modification and "p" designates a 3' phosphate modification. The nicking enzyme recognition site is indicated in bold.

Next will be described Example 1, which shows adjustment of the PEN-DNA toolbox for microsphere-conjugated templates. Sequences used in the example are shown in the table of FIG. 2. Before Example 1, a review of the PEN-DNA toolbox will be given.

Figure 3:
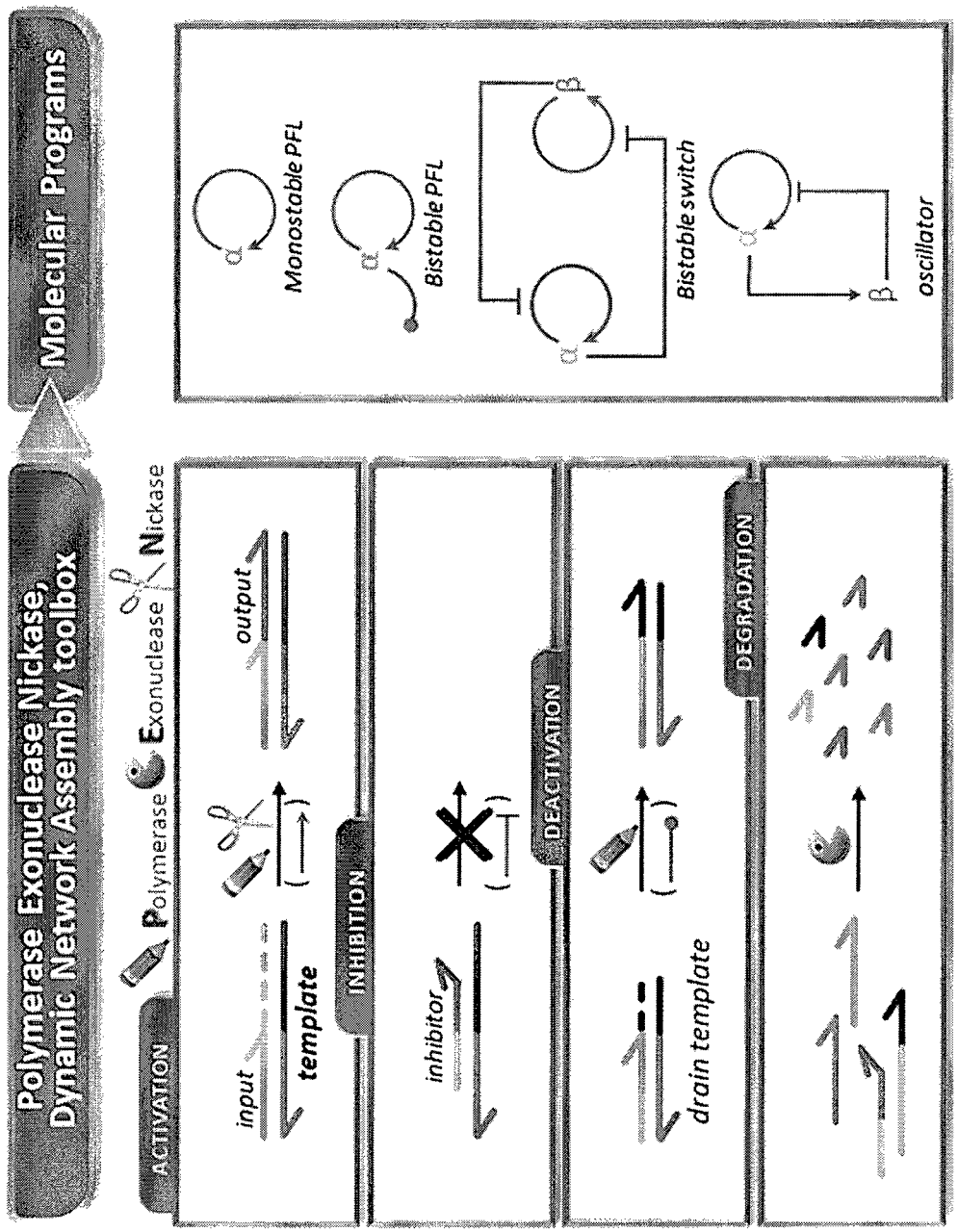
FIG. 3 is a set of schematic views of PEN-DNA toolbox.

FIG. 3 is a set of schematic views of PEN-DNA toolbox.

Figure 4:
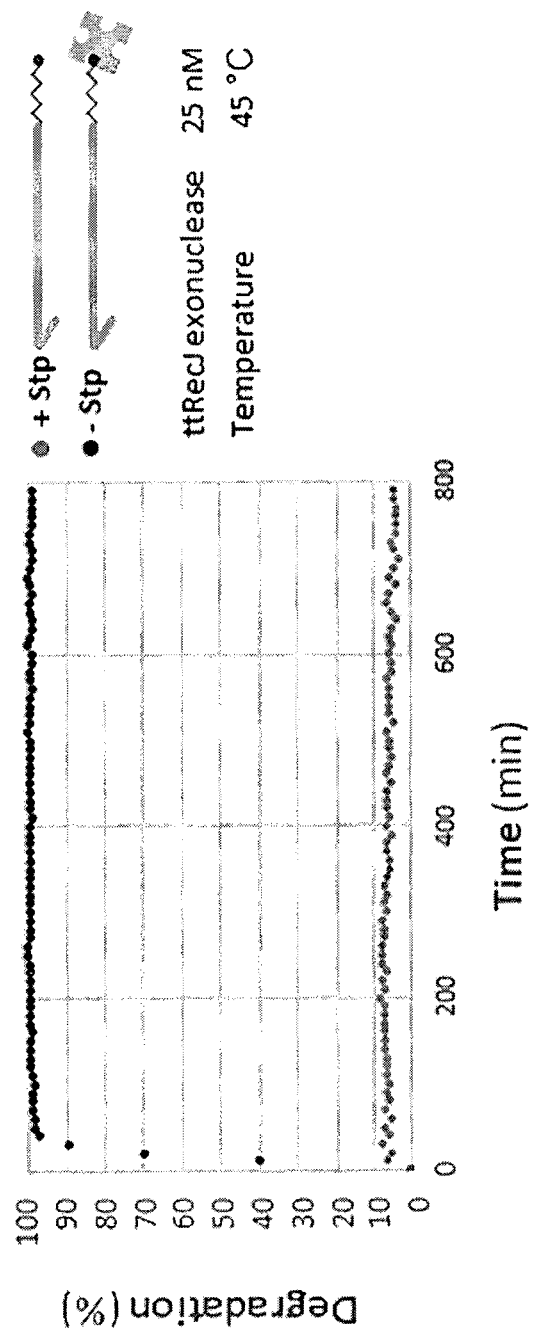
FIG. 4 is a set of schematic views showing experimental results of the degradation of free templates by an exonuclease.
Figure 6:
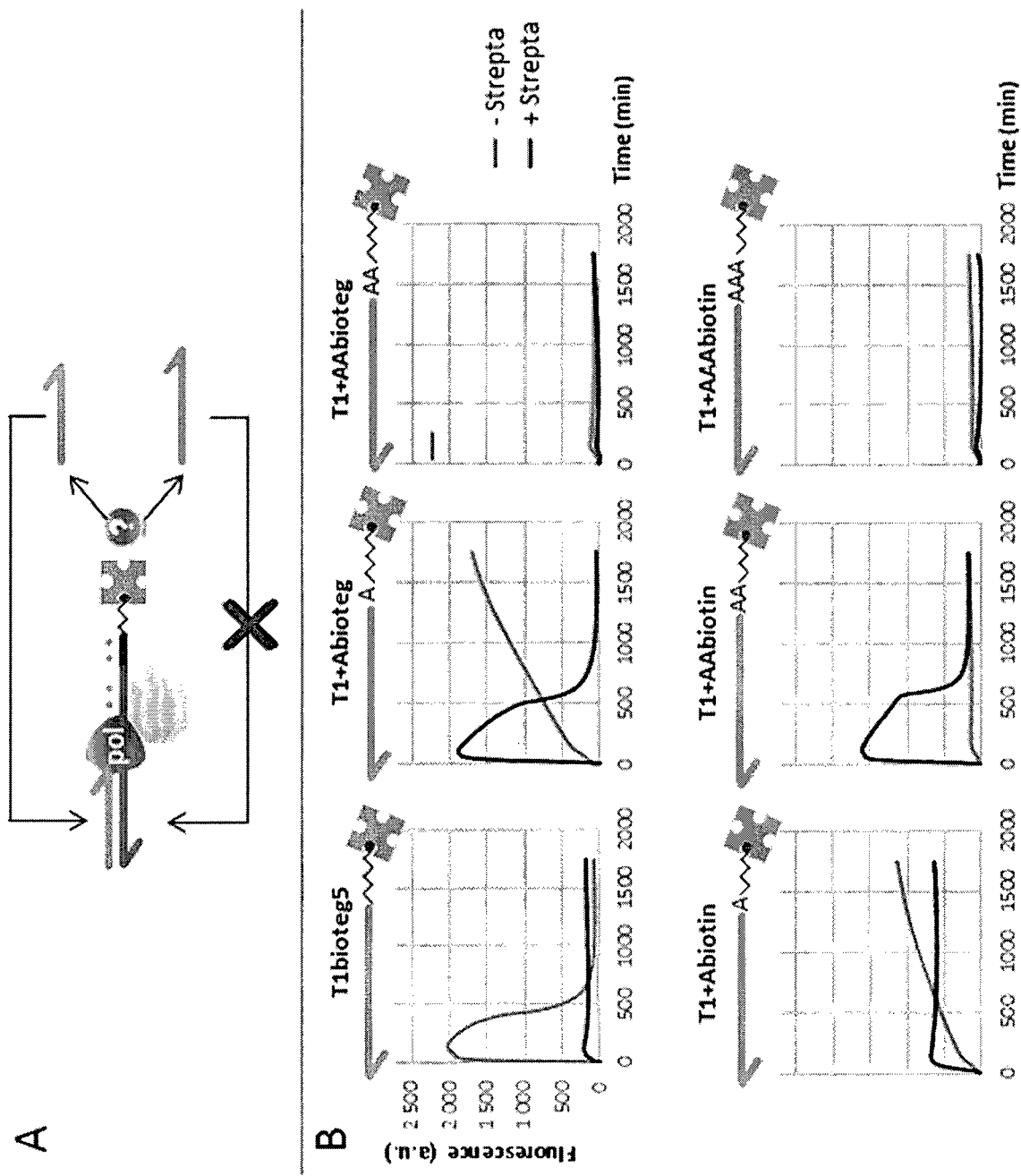
FIG. 6 is a set of schematic views showing interaction between polymerase and 5' streptavidin-conjugated DNA strands.
Figure 8:
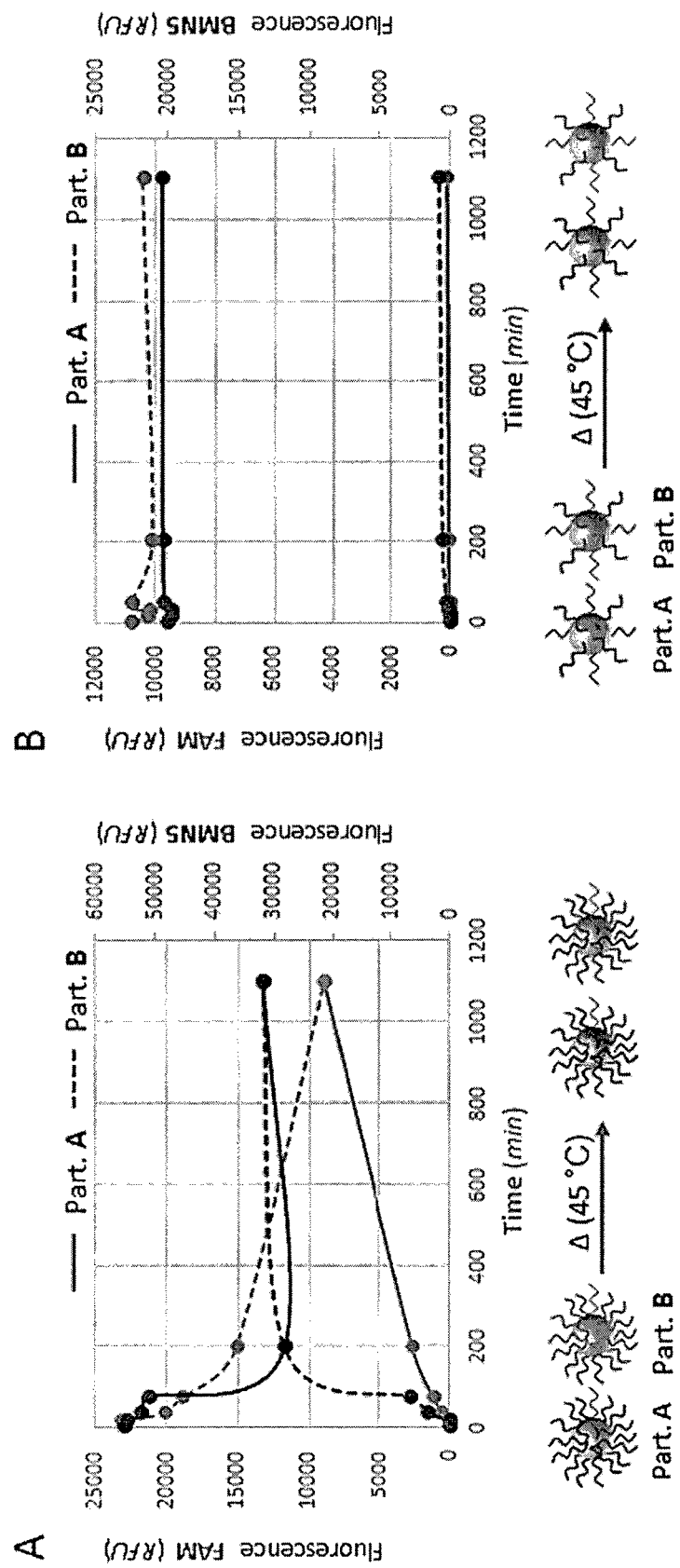
FIG. 8 is a set of schematic views showing kinetic of biotin-DNA exchange.

FIG. 4 is a set of schematic views showing experimental results of the degradation of free templates by an exonuclease. FIG. 5 is a first table showing experimental conditions in Example 1. FIG. 6 is a set of schematic views showing interaction between polymerase and 5' streptavidin-conjugated DNA strands. FIG. 7 is a second table showing experimental condition in Example 1. FIG. 8 is a set of schematic views showing the kinetics of biotin-DNA exchange on streptavidin-conjugated particles. FIG. 9 is a third table showing experimental conditions in Example 1.

The PEN-DNA toolbox provides a programmable way to design artificial molecular devices such as clocks, memories, logic elements etc. using DNA-encoded instructions as described in NPL 1, 2, 4 and 5. These systems perform as well-mixed molecular systems in test tubes held at a constant temperature in the presence of some enzymes. The PEN-DNA toolbox is a solution-phase biomolecular reaction-networking scheme where short synthetic DNA oligonucleotides are used to encode the connectivity information of the circuit. As shown in FIG. 3, the dynamic unfolds upon processing by a three-enzyme universal machinery: a DNA-polymerase elongates an input strand that hybridizes on the input side (3') of a matching template; a nickase site-specifically cuts the resulting full duplex, releasing both the input and a new output. The exonuclease unspecifically degrades all unprotected oligonucleotides (i.e. everything except templates), maintaining the system in a responsive out-of-equilibrium state. The cascading of the different modules (activation, inhibition, deactivation) allows the building of molecular programs and circuits.

Example 1 regards adjustments necessary to adapt the PEN-DNA toolbox for porous microsphere-supported format. Enzymatic activity on immobilized DNA substrates was intensively studied and reported in the literature and it was shown, for example, that tethered DNA primers are typically less active in solid-phase PCR (Polymerase Chain Reaction) than in solution phase PCR, due to thermodynamic (DNA hybridization), kinetic (enzyme and products diffusion), and spatial (steric hindrance) constraints (see, for example, NPL 18, 22 and 23). As a starting point to evaluate the possibility of transposing the DNA toolbox on a solid-supported format, the influence of the streptavidin/biotin linkage at the end of DNA templates on the PEN-DNA toolbox chemistry was studied, as a model of tethering. A basic exponential amplification program running with a single dual-repeat amplification template (the input strand and the output sequences are the same) was used to characterize the reactivity of the system (FIGS. 4, 6 and 8). This set of experiments was used to define the critical parameters (template orientation and length, functionalization density, and enzymatic parameters) most susceptible to yield proper performance for PEN-DNA programs in solid-supported format.

We first show that streptavidin protects 5'-biotinylated template from degradation by RecJ exonuclease, even in the absence of other modifications: Molecular programs working in batch conditions, such as those described in NPL 1-5, 24 and 25, use an exo(ribo)nuclease activity that guarantees time-responsiveness of the system by degrading produced species. The PEN-DNA toolbox in particular uses a thermostable 5'→3' single strand-specific exonuclease called ttRecJ (NPL 26). Therefore, templates have to be protected, or they would be digested by the enzyme. In the context of the PEN-DNA toolbox, templates are typically protected by site-specific incorporation of phosphorothioate backbone modifications in their 5' extremity, previously used in antisense oligonucleotide synthesis to provide nuclease-resistance (NPL 27). Other backbone nuclease-protecting modifications are available, including but not limited to phosphotriester, boranophosphonate, alkylphosphonate, phosphoramidate, guanidinium, N-(2-aminoethyl)glycine (used for peptide nucleic acid synthesis), etc. Additionally, unnatural nucleotide modifications including 2'-O-methyl-nucleoside, 2'-fluoronucleoside, 3'→5' inverted nucleotide among others end-blocking adducts, 2'-O-4'-C methylene bridge (referred as Locked Nucleic Acids), etc. provide resistance against various nucleases (NPL 28-32). The stability of oligonucleotides modified with biotin/streptavidin linkage or nano/microparticle conjugation has also been demonstrated (NPL 33-35). Here, the effect of the template attachment on streptavidin on their processing by the exonuclease ttRecJ was evaluated. The following experiment was performed (FIG. 5 shows a table for experimental conditions).

An oligonucleotide (ODN1) having a single biotin modification at its 5' end, but no backbone or nucleoside modification, was attached- or not-to a streptavidin and incubated with the exonuclease. The progress of the reaction was followed through the fluorescent signal emitted by EvaGreen (even if this dye is mostly a double strand specific reporter, a detectable fluorescent signal is produced in the presence of the single stranded DNA templates, and decreases if those templates are digested). The result of this experiment, depicted in FIG. 4, demonstrates that free templates are quantitatively degraded by the exonuclease within 30 minutes, while streptavidin-bound templates are fully protected.

FIG. 4 illustrates that biotin moiety in 5' protects templates from degradation by exonuclease in the presence of streptavidin, even in the absence of other modifications. 100 nM of template with a 5' biotin modification is incubated with or without streptavidin before being exposed to the exonuclease (ttRecJ). The template alone is quantitatively degraded by the enzymatic activity while the template linked to streptavidin is fully protected. This result demonstrates the protection of oligonucleotides by the 5'biotin/streptavidin linkage toward exonuclease activities. This result is valid for all types of 5' biotin modification tested and directly transposable to templates immobilized on streptavidin-coated microspheres, meaning that they are also protected if they are attached through a 5' biotin modification. This result is consistent with previous studies that demonstrate the stability of biotin/streptavidin-modified oligonucleotide toward cellular nucleases.

Second, we show that a 5' spacer before the biotin moiety is required for the complete extension of inputs on 5' biotin-streptavidin templates: The effect of the immobilization of templates via their 5' end on the polymerase efficiency was investigated. To that purpose, an indirect assay using a dual-repeat sequence T1 was devised (FIG. 6A). This sequence is used as template for the polymerase/nickase-mediated exponential amplification of the complementary sequence (a, CATTCTGACGAG, SEQ ID NO: 15). The amplification of the autocatalytic species a is monitored in presence of a small amount of dNTPs. The fluorescence signal corresponding to a shows an amplification profile with first an exponential amplification phase followed by a plateau (that corresponds to the steady state where the production of triggers equals their degradation by the exonuclease ttRecJ). Finally the depletion of dNTPs leads to the end of reaction and the return to initial level (no more production, only degradation). The template T1 is extended with 0 to 3 deoxyadenosines ahead of the biotin moiety (bioteg or biotin) located on its output side (5' end) (FIG. 6). FIG. 7 shows a table for experimental condition. The amplification does not occur if the polymerase reads across the (poly) dA linker, due the production of 3' mismatched triggers that cannot prime further polymerization on other templates.

The result of this experiment shown in FIG. 6B demonstrates that the template T1, without any extension (Tibioteg), amplifies well in absence of streptavidin while the reaction does not occur if the template is bound to a streptavidin. This observation suggests that the polymerization is incomplete on a tethered template and leads to a truncated output that possesses a melting temperature too low to bind efficiently the template. However, an exponential amplification profile is observed if one or two dA are added as linkers ahead of the bioteg and biotin moiety, respectively. An additional dA leads to inhibition of reaction in both cases, suggesting that the polymerase incorporates an extra, mismatching dT in these cases. Taken together, these results demonstrate that the polymerase misses (at least most of the time) one or two nucleotides if the template is tethered to streptavidin through a bioteg or biotin linker, respectively.

FIG. 6 illustrates the steric interaction between the polymerase and 5'-streptavidin groups blocking the polymerization for the last nucleotides of the template. FIG. 6A shows a schematic representation of the indirect assay used to determine how many nucleotides the polymerase misses when templates are conjugated to streptavidin. From this assay, it is determined that the polymerase misses (at least most of the time) the last one or the last two nucleotides if the template is tethered through a bioteg or biotin linker, respectively.

Here we evaluate the kinetic stability of the biotin/streptavidin link joining templates to porous microspheres: Bond stability between oligonucleotides and microsphere is critically important to guarantee the localized computation and amplification, especially in the case of multiplex assays, because each bead type has a different set of attached DNA strands and barcodes and exchange of DNA strands would lead to the homogeneization of the beads population. The biotin/streptavidin linkage is widely used by virtue of its ease of use and its high association constant ($10^{15}$ $M^{-1}$). However, the affinity decreases when large substituents are attached to the biotin moiety and the bond remains reversible compared to other covalent chemistry. It has been shown that biotinylated molecules can dissociate from the protein upon specific conditions (see, for example, NPL 36 and 37).

In order to study the stability of the biotin/streptavidin link used to attach DNA on particles in the context of the transposition of the PEN-DNA toolbox to a particle-supported format, two batches of streptavidin-modified microspheres were functionalized with two different fluorescent oligonucleotides. Here and in the rest of the description we used commercially available Sepharose resin, consisting of streptavidin-modified particles with a mean diameter of 34 μm, made of cross-linked agarose, but it should be understood that any other porous particles could be used. The two batches were then pooled and the kinetic of the exchange of conjugated templates at 45° C. was then investigated by flow cytometry (experimental conditions are shown in a table of FIG. 9). The result of this experiment shows that, if particles are saturated with templates (i.e. an excess of templates has been used during bead functionalization), the latter tends to exchange relatively rapidly, translating into the fluorescence equilibration of both beads batches (FIG. 8A illustrates kinetic of biotin-DNA exchange for saturated streptavidin-conjugated particles.). On the contrary, when the functionalization level is below the saturation level (i.e. a significant fraction of the streptavidin binding sites on each bead remains free), template exchange phenomenon is not observed. This is supported by the stability of fluorescence signal for both functionalized microspheres (FIG. 8B illustrates kinetic of biotin-DNA exchange for unsaturated streptavidin-conjugated particles). This result is probably explained by the fact that, only in the sub-saturated case, a biotin-related template that would detach from one binding site can be quickly recaptured by other available streptavidin sites present within the bead volume, before it is able to diffuse away from the particle. Another explanation would be the high repulsive forces undergone by negatively charged oligonucleotides in a saturated level of functionalization that would be less critical when decreasing the grafting density.

As a conclusion, it is important to graft the microspheres with a limited, non-saturating amount of biotinylated oligonucleotides to prevent inter-particle exchange during incubation. For the following experiment, CompuSpheres are functionalized with a total less than 2 nmol of oligonucleotides per milligram of particles (whereas the saturation level is around 3.3 nmol per milligram particles). It must be noted that other options are available for the tethering of templates on the solid support, such as dual biotin modification of the template, which are classically used for solid-state PCR applications using streptavidin-modified support (see, for example, NPL 20). Alternatively many DNA attachment chemistries are known to attach DNA on supports using for example covalent linkages (NPL 13, 14 and 18). These options could be readily adapted to the present context to avoid any exchange of strands between particles. Finally, it is also well known that non-polymerizable spacers, such as polyethylene spacers or aliphatic spacers can be used to link two oligonucleotides, which then act as independent substrates for the polymerase (for such constructions, see NPL 38 and 39 and patent document U.S. Pat. No. 8,252,558 B2). Therefore, instead of being directly attached to the surface of the microsphere, some modules could be attached to the free end of other tethered modules using such spacers.

Next will be described Example 2, regarding running of a basic polymerase-nickase amplification system localized on porous microsphere.

Figure 10:
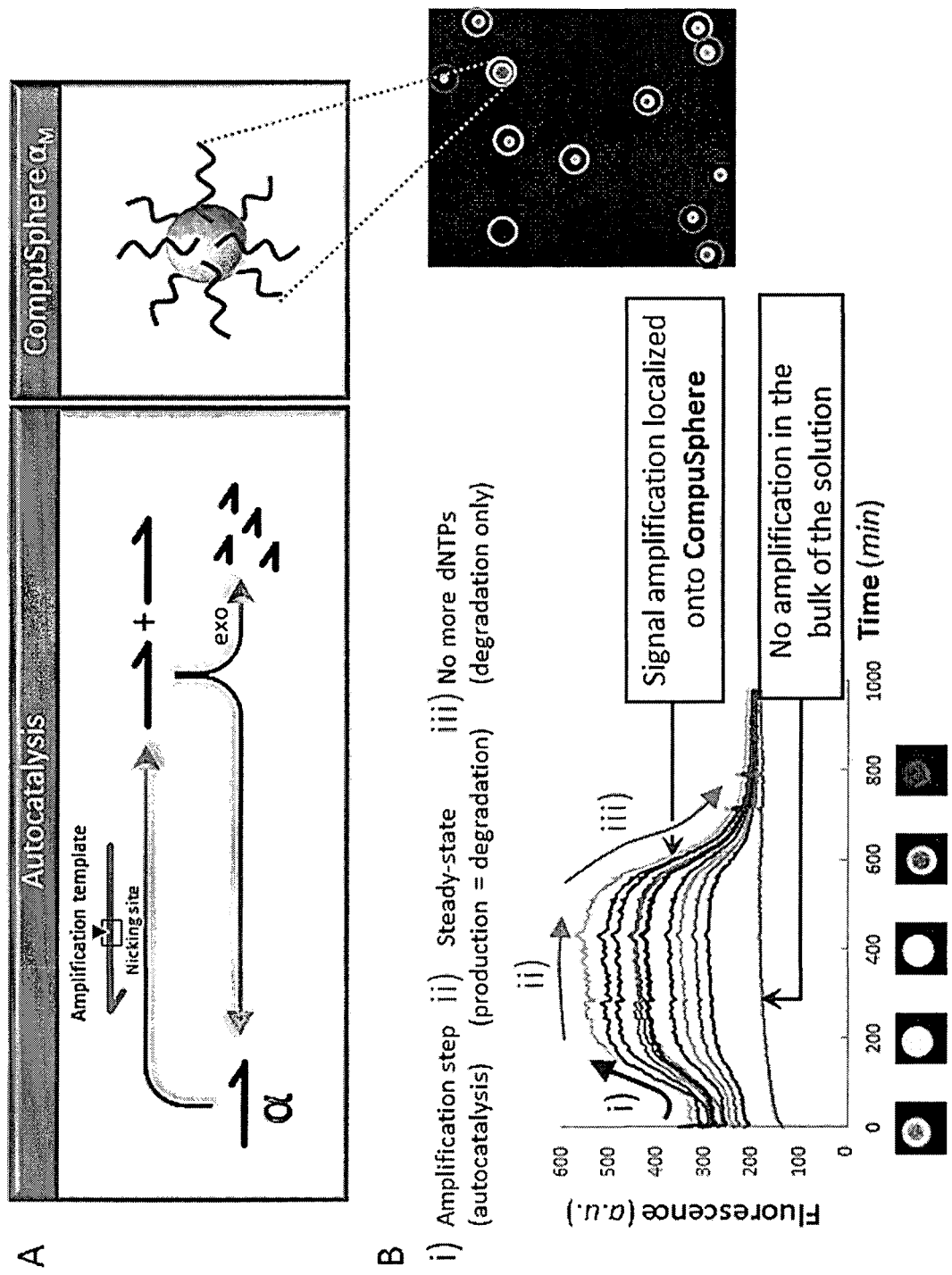
FIG. 10 is a set of schematic views showing the implementation of an autocatalytic loop on CompuSpheres.
Figure 12:
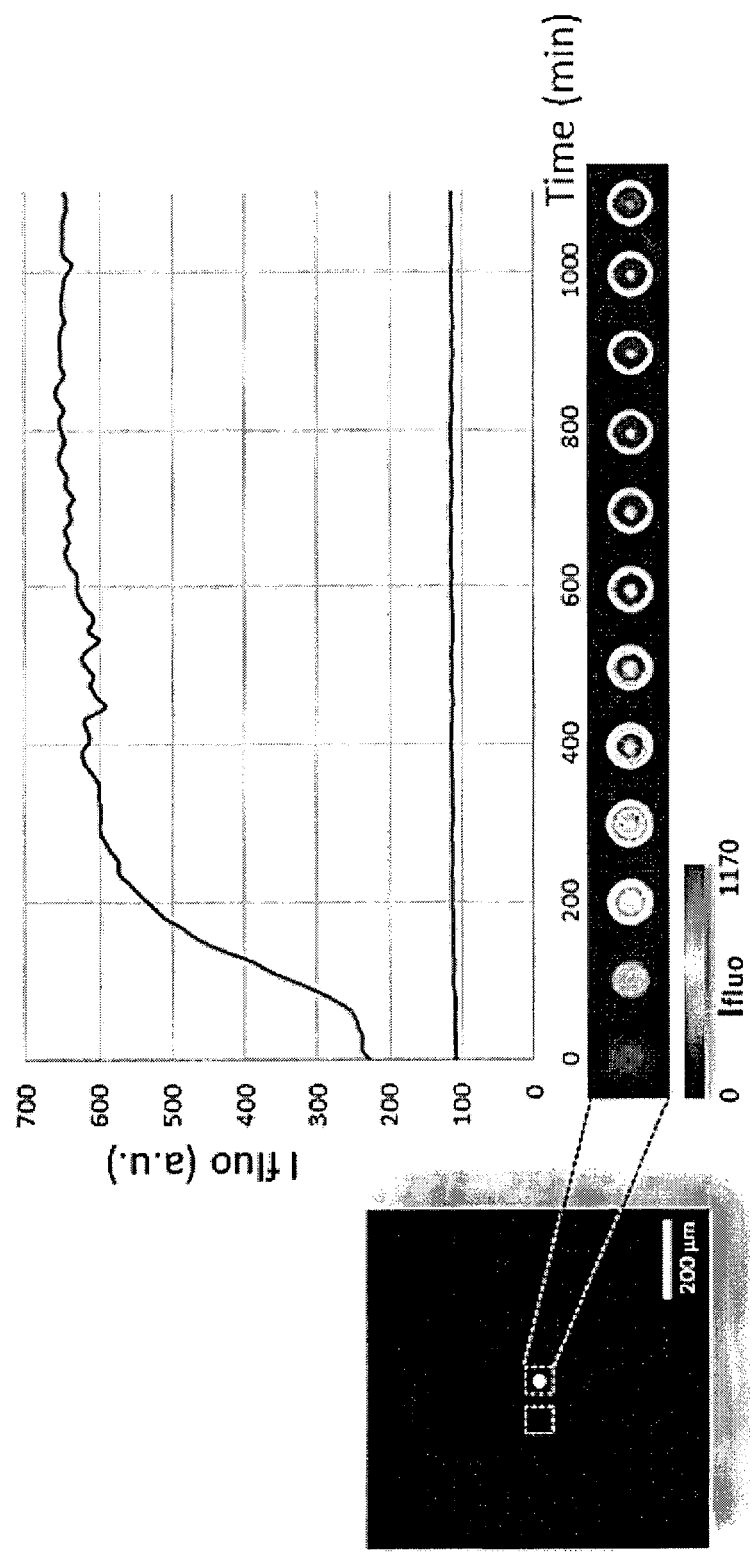
FIG. 12 is a set of schematic views showing autocatalytic loop on CompuSpheres.

FIG. 10 is a set of schematic views showing the implementation of an autocatalytic loop on microspheres. FIG. 11 is a first table showing experimental condition in Example 2. FIG. 12 is a set of schematic views showing autocatalytic loop on microspheres. FIG. 13 is a second table showing experimental condition in Example 2.

In this example, it is evaluated whether microsphere-supported templates perform qualitatively identically as templates in their free-diffusing form (i.e. in a homogeneous solution). It is further shown here that the amplification reaction happens only within a very small fraction of the total solution volume, which is mostly the volume contained within the spheres, in contrast to classic solution based approaches, where amplification reaction is distributed homogeneously over the entire volume of the reaction. Moreover, it is shown that, despite the fact that they are made of porous material open to the solution, the template-grafted microspheres behave autonomously in the solution and can maintain their active state in the face of diffusion, even when a unique microsphere is present in a system of a few microliters and thus the active volume where the reaction is localized is less than $\frac{1}{10}^6$ of the total sample volume.

Experiment:

A simple system encoded by a single template called αtoα was selected (Bioteg* C*T*C*G*TCAGAATGCT CGTCAGAATp, SEQ ID NO: 10 * and p denotes a phosphorothioate bond and 3' terminal phosphate, respectively). Because this template has a repeat structure and contains the nicking enzyme recognition, it is well known that, when incubated in the presence of a polymerase and the nicking enzyme and dNTPs, and in the correct buffer, salt and temperature conditions, it will lead to the exponential amplification of its complementary sequence a (CAT TCT GAC GAG SEQ ID NO: 15) (FIG. 10A) (cf. patent document WO 2004067726 A3 and NPL 40). Moreover, it has been reported that, when the reaction is performed in the additional presence of an exonuclease (and assuming that the template is protected from degradation by the exonuclease), the reaction reaches a plateau and remains stable, until all dNTPs are exhausted from the solution. The DNA-production reaction is then not sustained anymore and the concentration of a goes back to 0, while the templates return to their single-stranded state. Fluorescent reporters can be used to follow the progress of the reaction and, therefore, one expects to see a characteristic amplification/plateau/return-to-the-base-line shape for the fluorescence signal (see, for example, NPL 2).

Thus the biotinylated amplification template αtoα was attached to the streptavidin-modified Sepharose beads by incubating 300 pmol of template with 5 μL of the stock suspension of microspheres under continuous agitation for 15 minutes in a high ionic strength binding buffer (Tris-HCl pH7.9 20 mM, EDTA 10 mM, NaCl 1M, Tween20 0.2%). Functionalized CompuSpheres ($CS\alpha_M$) are then washed and stored in an appropriate buffer up to 6 months (Tris-HCl, pH 7.0, 2 mM $MgSO_4$, 100 mM NaCl).

Next, approximately, 103 microspheres are poured in the reaction mix obtained by combining the components according to the table of FIG. 11. It must be noted that given the strong link between biotin and streptavidin, and as demonstrated in the previous example, no or at least very little template is expected to be free in solution: the overwhelming majority of templates are bound to the microspheres. A double strand specific dye (Evagreen) is introduced to allow a fluorescent monitoring of the reaction. This compound produces a bright green fluorescent signal in the presence of double stranded DNA, and limited fluorescence in the presence of single-stranded DNA or monomers such as dNTP and dNMP.

The mixture of microspheres and reaction mix is then introduced in an incubation chamber made in-between two microscope coverslips separated by a spacer and sealed with epoxy adhesive (Araldite®). This incubation chamber is transferred to an Olympus IX71 inverted microscope equipped with a CoolLED illumination source and an iXon3 897 EM-CCD camera (Andor). The temperature of the incubation chamber is maintained at 45° C. thanks to a transparent thermoelectric heating plate (Tokai-Hit). Time lapses are recorded using a 2× or 4× objectives magnification through the open source microscopy software μManager 1.4.

FIG. 10 illustrates the behavior of the autocatalytic loop on microsphere, where a microsphere is functionalized with an amplification template that encodes a positive feedback loop (autocatalysis) leading to DNA amplification when incubated in the presence of a polymerase, a nickase and dNTPs. The microspheres are contacted with a mixture of polymerase, exonuclease, nickase activities and incubated at 45° C. The reaction is monitored by fluorescence microscopy with a double strand specific dye (Evagreen). The amplification profile (first order amplification, steady state and return at the initial stage after dNTPs exhaustion) demonstrates the proper running of the molecular program in the microsphere-supported format. The microspheres are therefore performing the function encoded by their decorating DNA templates.

Results:

FIG. 10B illustrates that $CS\alpha_M$ efficiently amplifies the a strand, which results in a sharp fluorescence increase. After an exponential phase, the signal reaches a stable plateau corresponding to the steady state (where the production of a by polymerase/nickase/template equals the degradation by the exonuclease). After dNTPs exhaustion, the production stops and the gradual degradation of the a strand brings the templates back to their initial single-stranded state, which result in a decrease of the fluorescence. It is important to note that the enzymatic reaction strictly occurs on the particles while no signal is observed in the rest of the solution (even if some of the produced single-stranded DNA strands are expected to diffuse away from the microspheres, they do not produce a detectable fluorescence signal). This result demonstrates the proper running of a simple amplification function localized within the bulk of the porous microspheres, in presence of the three PEN-DNA toolbox enzymatic activities (polymerase activity, nickase activity, exonuclease activity). It also demonstrates the reusability of the system, which goes back to its initial state when chemical fuel (dNTP) is depleted.

The same experiment is now repeated but the microsphere suspension is first diluted enough that a single microsphere is finally present in the incubation chamber (FIG. 12). FIG. 13 shows a table for experimental conditions. In this setting, CompuSpheres cannot receive compounds from neighboring beads and therefore any reactivity observed on the microsphere can be considered as an autonomous properties of that microsphere, not as a collective behavior of many microspheres. FIG. 12 illustrates that a unique CompuSphere is incubated in a large chamber and the fluorescence signal still reveals an exponential amplification localized on the microsphere.

The sharp signal increase observed in FIG. 12 illustrates that the programmed particle is able to autonomously perform the amplification reaction and sustain a high production rate for more than 18 hours. The behavior reproduces the one observed for multiple microspheres in the chamber, except that the return to the basal signal is not observed. This is because the single microsphere consumes dNTP much slower that the many-bead population can, and the high state can therefore be maintained for a much longer time. In any case, the sustained high fluorescence level demonstrates that the reactivity of template-grafted microspheres contacted with the enzymatic machinery is an autonomous property of each microsphere, not a population level behavior. It must be noted that Zhang et al. reported a result where isothermal polymerase-nickase based amplification of a short DNA strand was performed on a bead-supported format (NPL 41). However this work focuses on larger (80 micrometers) beads, grafted on their outer surface (not in their bulk) and used one by one (not as a collection of beads, as we show in the following examples). Moreover, the single bead in this case was grafted with a single DNA sequence, whereas the focus of the present invention is to attach a complete molecular program, that uses local exchange between multiple DNA sequences to provide improved sensing capability (for example, background free detection using a leak-absorption module, as shown in the following Example 3, or re-programmable detection using additionally a target-conversion module, as shown in Example 5).

Next will be described Example 3, regarding the fact that a more complex molecular program, using more than one module, can also run in a microsphere-supported format. Specifically, we show that CompuSphere grafted with a bistable program based on two templates can be used to report on the presence/absence of specific nucleic acids while avoiding background amplification.

Figure 14:
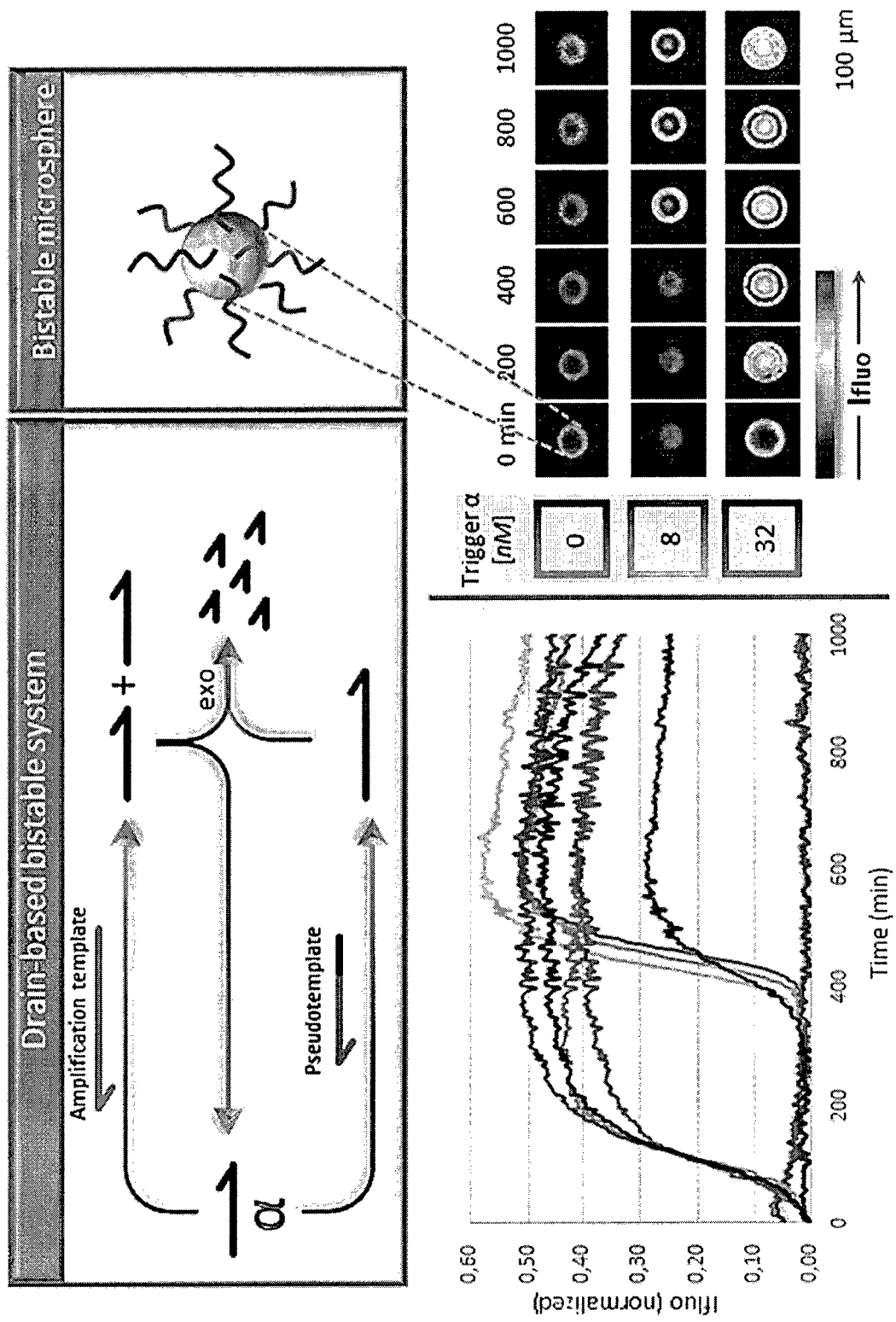
FIG. 14 is a set of schematic views of detection of the presence/absence of DNA strand.

FIG. 14 is a set of schematic views of detection of the presence/absence of a DNA strand. FIG. 15 is a table showing experimental conditions in Example 3.

It is well known that isothermal polymerase-nickase amplification systems display a background amplification, in the sense that even in the complete absence of initial trigger, an exponential amplification is eventually observed (see, for example, NPL 42 and 43). This limits the usability of these systems, as well as many other isothermal DNA amplification schemes, for the detection of nucleic acids. However, this can be managed by the use of molecular programming techniques: to avoid the background amplification phenomenon, porous microspheres were programmed with a bistable molecular program requiring two strands: the first module is an amplification template showing a partial repeat structure (αtoα) complementary to the sequence of interest (α), while the second is a leak-absorbing template (pTα), which absorbs the leak reaction from the autocatalytic template and allows the adjustment of the amplification threshold (FIG. 14). Absorption of the leak is obtained because the leak-absorbing template reacts faster with the amplified input/output DNA strands and converts them to an inactive form, but is present in lower concentration. The exonuclease present in the solution, along with the polymerase and nickase, is used to process the wasted products. Using this design, autocatalytic amplification can start only when the leak-absorption capacity threshold is crossed. It is therefore expected to obtain each microsphere as a bistable unit that stays in the OFF state in absence of target as a triggering event. However, upon target exposure (at a concentration exceeding a certain threshold), we expect that the supported template will catalyze the amplification resulting in sharp fluorescent increase and that the microspheres will switch to a stable ON state indicating detection.

Experiment:

Bead functionalization: The two biotinylated DNA template (300 pmol αtoα, Bioteg* C*T*C*G*TCAGAA TGCTCGTCAGAATp SEQ ID NO: 10) and leak-absorbing template (100 pmol pTα, Biotin*A*A*AAAACTCGTC AGAATGp SEQ ID NO: 13) are mixed (3:1 ratio) in a binding buffer (Tris-HCl pH7.9 20 mM, EDTA 10 mM, NaCl 1M, Tween20 0.2%). Sepharose beads are introduced with immediate vortexing (5 µL from the stock suspension, 300 µg). The functionalized particles ($CS\alpha_B$) are washed and stored at 4° C. for up to 6 months in the storage buffer.

Reaction assembly: three different reactions are assembled by introducing the $CS\alpha_B$ in the master mix (reaction buffer+enzymes, shown in a table of FIG. 15) supplemented with 0, 8 or 32 nM of target (α, CAT-TCTGACGAG, SEQ ID NO: 15).

Reaction monitoring: Each of the three samples is heated at 45° C. and imaged by time-lapse epifluorescence microscopy using the double-strand specific dye Evagreen (see Example 2). The fluorescence signal of each bead indicates the progress of the amplification reaction. A low fluorescence signal corresponds to the "OFF" state, when the autocatalytic reaction is below the threshold and does not amplify the signal. On the contrary, a sharp fluorescence increase corresponds to the amplification reaction bringing the CompuSphere to its "ON" state, which is then sustained for a very long time (if sufficient dNTP is included in the buffer, see Example 2).

Results:

FIG. 14 illustrates the results of the experiment. Specifically, FIG. 14 illustrates detection of the presence/absence of a DNA strand using microspheres functionalized with a mixture of amplification template and leak-absorbing template ($CS\alpha_B$). The part A (the uppermost part) illustrates principle of the detection scheme. The part B (the lower left part) illustrates time traces obtained for three samples: $CS\alpha_B$ are incubated with the reaction mix supplemented with 0, 8 or 32 nM of target strand a, respectively. The part C (the lower right part) illustrates fluorescence images b and (a). In absence of target, CompuSpheres stay in their inactive state, reporting an "OFF" response. If the target is added in the reaction mix, CompuSpheres sense its presence and amplify the sequence, leading to a shift to a strong fluorescence state ("ON" state). As illustrated in FIG. 14, in absence of target (0 nM a), CS $\alpha_B$ stays in the "OFF" state for up to 1000 minutes. If the target is introduced in the sample (32 nM), the threshold is exceeded and the microspheres switch "ON" and emit a strong fluorescence signal. At an intermediate concentration of target (8 nM a), CS switch to the "ON" state with a delay (about 400 minutes). As a conclusion, microparticles embedding a bistable program are able to detect the presence of a specific target and display the corresponding fluorescent response without being sensitive to background amplification in the absence of target.

Next will be described Example 4, regarding multiplex assay for the simultaneous detection of two single-strand DNA targets present in the same sample.

Figure 16:
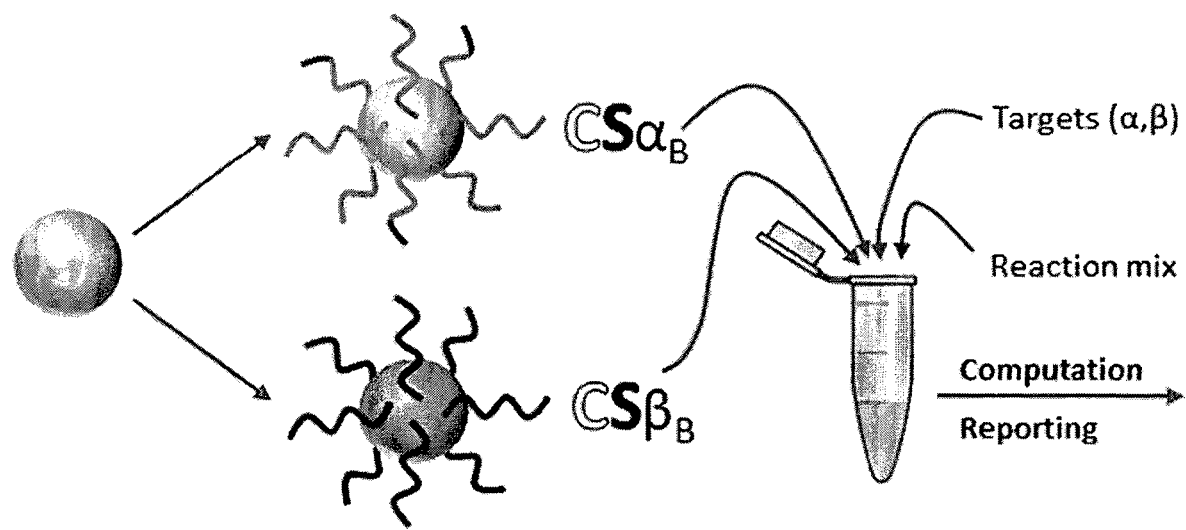
FIG. 16 is a set of schematic views of duplex assay for simultaneous detection of detection of a and 8 strands.
Figure 16:
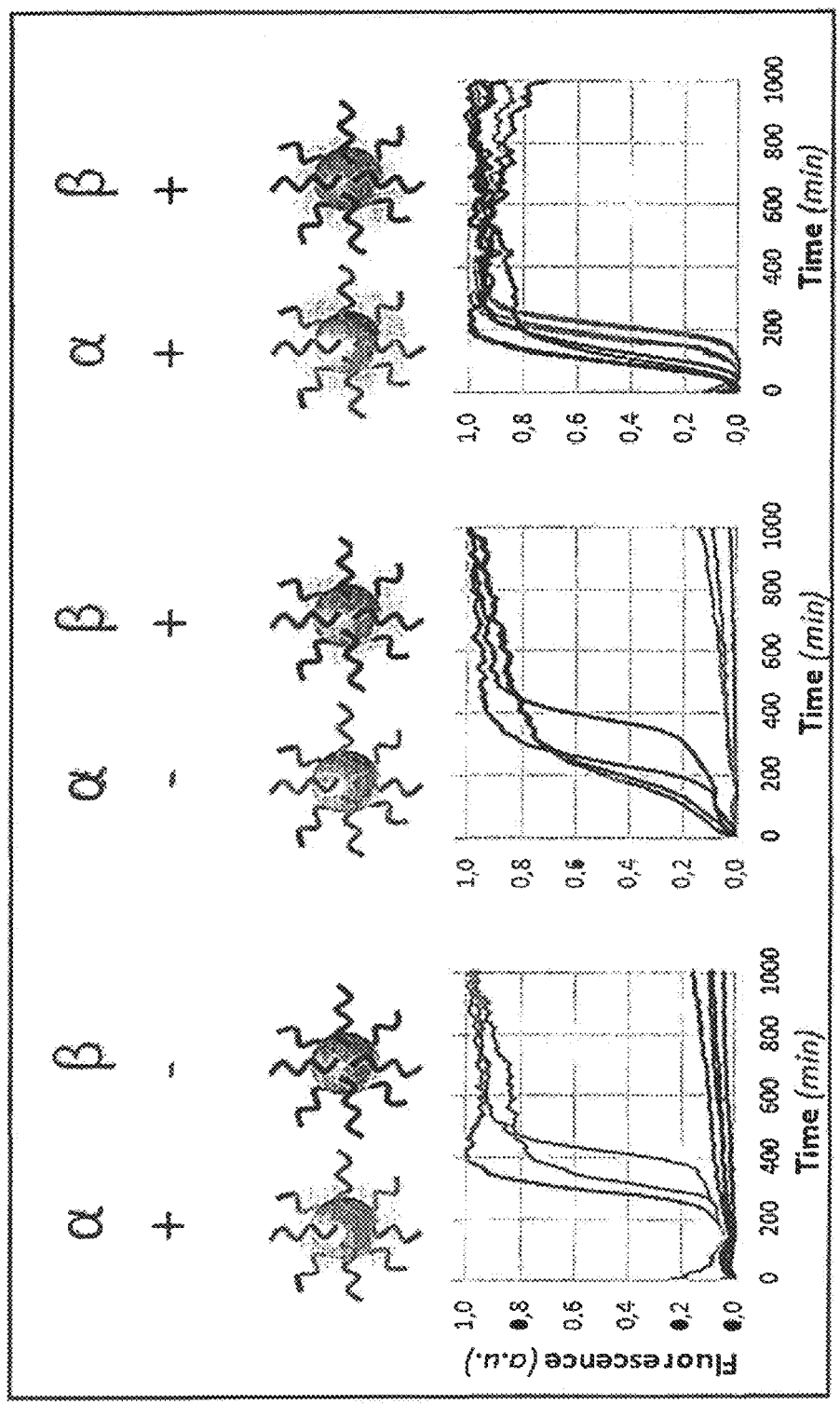

FIG. 16 is a set of schematic views of duplex assay for simultaneous detection of a and ß strands. FIG. 17 is a table showing experimental conditions in Example 4.

The detection of several targets within the same sample is of great importance for clinical diagnostic, for instance to assess the pattern of expression of pathological biomarkers associated to a cancer type or a genetic disease. CompuSpheres are suitable for such purpose since they can have different molecular programs on different particles but perform independently in the same solution. Each particle type is specifically designed to detect autonomously and individually the presence/absence of a different target molecule and to report this information using a fluorescent signal. Additionally, different CompuSpheres carrying different tasks can be made easily distinguishable with the use of fluorescent barcodes and therefore can use a unique readout channel (in contrast to multiplex assays using spectrally resolved fluorescent reporters, limited to four to five targets).

Experiment:

As an example of multiplexing, two different programs were implemented using two distinct CompuSpheres populations, shown in a table of FIG. 17: one sensing a strand called a (CATTCTGACGAG, SEQ ID NO: 15) while the other is designed to sense a strand called ß (CATTCAG-GATCG, SEQ ID NO: 16). It is often the case in diagnostics that two targets are quite similar in sequence. Here ß is designated with a sequence similar to a but a few mismatches. Each particles population is barcoded with a fluorescent dye during the synthesis (by co-grafting a biotin labeled fluorescent oligonucleotide) so that they can be differentiated using their fluorescent properties. After synthesis, both microsphere types are pooled together and exposed to a sample containing either: no input; α only; ß only; both α and ß.

Results:

FIG. 16 illustrates that each programmed particle can be distinguished using its fluorescent barcode, detects independently and specifically the presence/absence of its target strand and adopts the expected "ON" (in presence of the cognate target)/"OFF" state (in absence of trigger). As illustrated in FIG. 16, two CompuSpheres batches are synthesized; one functionalized with a bistable module that senses a, the other embedding a bistable module whose input is B. The two CompuSpheres populations are separately barcoded, pooled together, supplemented with the reaction mix and exposed to the target(s). The computation of each bead is monitored by fluorescence microscopy. It appears that for each experimental condition, the system efficiently reports the absence (CS "OFF" state) or the presence (CS "ON" state) of the corresponding target. This result demonstrates that simultaneous measurements of various targets can be performed using differently programmed microspheres in the same solution. This highlights the potential for massive multiplexing capabilities of CompuSpheres because it shows that different microspheres can perform different tasks while being immersed in the same solution.

Next will be described Example 5, regarding coupling of a two-module bistable motif (background-free amplification) to a target-conversion module (detection).

FIG. 18 is a set of schematic views of CompuSpheres embedding a bistable system (amplification module+leak-absorbing module) and a target-conversion module. FIG. 19 is a table showing experimental condition in Example 5.

A huge advantage of colocalizing the detection and the amplification on a microsphere whose volume is much smaller than the sample to be assessed is that one can conceive a versatile design composed of a single amplification loop (and a unique readout) coupled to a variety of target conversion module, each designed for a different target and being attached a different CompuSphere type. Moreover, using the barcoding strategy presented above the different sensing assay can be performed at the same time and in the same solution.

Experiment:

To demonstrate this principle, CompuSpheres CSß$_B$ bearing a bistable module (amplification template ßtoß Biotin*C*G*A*TCCTGAATGCGATCCTGAAT-p, SEQ ID NO: 11) and leak-absorbing template pTB, Biotin*A*A*AAAACGATCCTGAATG-p, SEQ ID NO: 14) were synthesized. Particles are subsequently supplemented with a target conversion module (template αtoß). These particles are named CSα→ß$_B$. CSß$_B$ and CSα→ß$_B$ are separately incubated in the reaction mix (shown in the table of FIG. 19) containing 0 or 10 nM of the target a and the reaction is monitored by fluorescence microscopy at 45° C.

Results

FIG. 18 shows that CompuSpheres embedding a bistable module (ßtoß and pTß) and a target-conversion module (αtoß) are able to detect the presence of the targeted strand (error bars are represented in graphs). On the contrary, CompuSpheres CSßB without the target-conversion module are insensitive to the presence of the target (a strand). This is because only the colocalized target-conversion module is able to capture the target and uses it to trigger locally the switch of the bistable module, resulting in the observation of amplification on the particle CSα→ß$_B$ (going to the "ON" state). As a negative control, in absence of target, both CompuSpheres remain in their "OFF" state for more than 500 minutes. This result can be extended to design other target-conversion modules for different targets, in order to create a highly multiplexed assay.

Next will be described Example 6, regarding specific reporting of the computation.

FIG. 20 is a set of schematic views showing experimental results of target detection with CompuSpheres grafted with a specific reporter strand. FIG. 21 is a table showing experimental conditions in Example 6.

Classical (single plex) RT-PCR assays or isothermal amplification methods (EXPAR, LAMP, RCA) rely on a fluorescence readout that typically uses double strand selective dyes such as SyBRGreen or Evagreen. However, specific reporters such as Taqman probes and their derivative are used to allow multiplexing or to increase the specificity of the assay. Here it is shown that a specific colocalized fluorescence reporting strategy can be used for the microsphere-supported assays.

Experiment:

In the present case, beside the target-specific molecular program, a reporter strand is added during the CompuSphere synthesis (FIG. 20A). This reporter strand is composed of the stem-loop structure extended with a 5' polyT tail ahead of the biotin moiety. Both extremities of the stem are modified with a fluorophore and a quencher. The loop is complementary to the trigger of the bistable module. Once the trigger binds the loop, the stem is destabilized and the trigger is elongated by the polymerase. This irreversible step keeps the fluorophore away from the quencher, resulting in an enhanced fluorescence emission. Microparticles (CSα→ß$_{BR}$) are functionalized with the 4-strand program (amplification template, leak-absorbing template, target-conversion template and the reporter, shown in a table of FIG. 21). After washing, CSα→ß$_{BR}$ are incubated at 45° C. with the enzymatic machinery and a concentration of target a ranging from 0 to 10 nM. The reaction is monitored by fluorescence microscopy through the red channel (Cy5 emission fluorescence).

Results:

FIG. 20 illustrates the results of the microscopy experiment for four samples (target concentration=0, 0.1, 1 and 10 nM). Specifically, FIG. 20A is a schematic illustration of CompuSphere embedding a 4-strand program (CSα→ß$_{BR}$). FIG. 20B illustrates a mechanism using the dye/quencher probe R8. FIG. 20C illustrates time traces and error bars for four samples: CSα→ß$_{BR}$ are incubated together with the reaction mix and the target (0, 0.1, 1 or 10 nM of α). And FIG. 20D shows fluorescence images for one CompuSphere of each sample. In absence of target, CSα→ß$_{BR}$ stay in the OFF state and exhibit a low fluorescence level for more than 1000 minutes, demonstrating that the reporter, even attached on the particles do not impact the performance. We observed the same results (beads stay "OFF") for 0.1 nM of target, suggesting that the threshold is not exceeded during this experiment. On the contrary, CompuSpheres report a positive signal where they are triggered by 1 and 10 nM of a strand. The reporting strategy implemented in this experiment shows that the generation of a specific fluorescent signal is possible, with a generic design strategy applicable to any amplified sequence. It is clear that many other fluorescent reporting strategies are a priori compatible with the microsphere approach presented in the present embodiment.

Next will be described a discussion about issues that the present embodiment would solve.

In molecular programming, the computation is performed by molecules floating freely in the solution. Integration of independent calculations in the same environment is challenging since unwanted interactions (in particular competition for enzymatic resources, as seen in many biomolecular protocols dealing with combinations of reactions) may arise and multiple readout is limited. The present embodiment is conceptually different from previous solution-based approaches, as programmed particles are separately implanted with the desired molecular program and individually perform the computation. Compared to their solution-phase counterparts, programmed particles of the present embodiment offer the following (a)-(e) advantages:

(a) Easy handling and storage of molecular programs
(b) Rapid and simple buffer exchange
(c) Program reusability
(d) Miniaturization and parallelization
(e) Multiplexed operation and reading (using for example fluorescent barcodes)

Other miniaturization and parallelization techniques mostly involve compartmentalization of reactions into droplets (NPL 44-47) or micro-chambers (NPL 48 and 49). These technologies have been developed industrially and are now commercially available (cf. Raindance™ Technologies and Droplet Digital™ PCR System from Biorad for droplet-based assays and Fluigdim® company for analysis in individual-reaction chamber). Although droplet-based techniques permit the rapid formation of thousands to millions compartments, they are ill-suited to the simultaneous fabrication of emulsion embedding many different programs due to the continuous flow process. Also, such methods require the generation of the microfluidic emulsion at the time of use and thus require complex equipment and are time consuming (chips fabrication, sample preparation, encapsulation). Besides, multiplexing is still challenging in droplet format since it requires multiple specific optically distinct probes (with distinct fluorescence emission wavelengths or intensities) and commercially available droplet technologies have a limited number of available fluorescent channels for readout.

The present embodiment removes the constraints linked to water-in-oil partitioning or microfabrication. Instead, the present embodiment provides the one-pot pre-synthesis of millions of "smart" microspheres with a precise control on the constituents and a high versatility (theoretically, any DNA-program can be designed and assembled onto porous particles). Multiplexing orthogonal molecular programs is also possible thanks to the parallel particle functionalization and barcoding and subsequent pooling in a mixed population that can be used in a common sample. Besides, particles can be easily handled and subject to various treatments or storage conditions (drying, freezing, buffer exchange . . . ), because they consist only of quite stable components (polymeric matrix, DNA). Only simple operations (contacting the microspheres with the sample and/or a processing buffer containing the enzymatic activities, incubating at constant temperature, centrifuging, washing and transferring the microspheres between solution) is left for the user who can still get the benefit of complex and parallel molecular programs running within each microsphere.

The molecular program can be designed to filter noise, have a given threshold of detection, detect patterns of inputs (instead of a single input), produce temporally defined responses (single peak, oscillations) etc., as already demonstrated for molecular programming in the solution-phase. All of these functions can be useful to create smarter and more efficient diagnostic tools.

Next will be described considered applications, such as biosensing applications for clinical purposes and others.

Biosensing Applications for Clinical Purposes:

Circulating free DNA (cfDNA) are important but challenging biomarker candidates because they are present at very low concentration in plasma. MicroRNA (miRNA) present in blood sample is also linked to various diseases. A sensitive, specific, robust and cheap detection scheme would make them valuable for clinical diagnostic.

For example in the case of miRNA, despite the complexity of understanding of miRNA regulation, fundamental research has established that each tissue expresses different miRNA sequences with heterogeneous level of production. Likewise, each cancer disease involves a variety of miRNA deregulation and thus exhibits a specific miRNA signature. From this observation, it appears primordial for clinical diagnosis, tumor classification and treatment to have highly multiplexed assays able to reveal miRNA expression patterns.

As a proof of concept, the present embodiment has already demonstrated that microspheres can be programmed to stay inactive for a very long time in the absence of a specific triggering signal and switch on their fluorescent signal upon specific target exposure, and that this can be done in parallel for multiple targets. This could be applied to the simultaneous detection of multiple miRNA in one biological sample, thereby enabling more robust diagnostic through the precise classification of the tumor miRNA pattern. Because molecular programming techniques allows to adjust the amplification threshold it is possible to adjust the sensitivity of each particle and thus have a large dynamic range of detection, even using only end-point readout. For example, 10 different types of target-detection CS for the same target, but with threshold going from nanomolar to 1 picomolar could be synthesized (each with a specific barcode signature to be easily distinguished), pooled together, used to test a sample. Readout would then reveal the actual concentration of the target, because all CS with lower thresholds would switch ON, whereas all CS with higher threshold would stay OFF.

Next will be given a discussion about relevancy, novelty and inventive step of the present embodiment.

It is the first time that molecular programs requiring multiple instructions are implanted on an integrated, porous microsphere platform, where each microsphere acts as an autonomous processor (in the presence of a set of enzymatic activities), and various types can be used in parallel. Previous studies based on DNA-decorated particles have used only either only one type of decorating strands (and thus, are not generally considered as molecular programs), or have required diffusion inbetween beads to perform (hence are not autonomous). For example, a previous study (NPL 50) has demonstrated the surface functionalization of particles by DNA computing elements, where computation is performed through a network of distinct particles (i.e. donor and acceptor particles). These particles are not able to autonomously sense, compute, and display readout but act collectively in a bulk solution. On the contrary, the present embodiment integrates both sensing and detection modules within mesoporous microspheres, and these modules cooperate locally within the microsphere so that each microsphere acts as autonomous sensing component (when immersed in the processing buffer). Zhang et al. reported the use of large DNA-functionalized magnetic particles for the detection of nucleic acid (NPL 41). This study is fundamentally different from the present invention in that the particle is surface-functionalized with a unique DNA strand that catalyzes the basic EXPAR reaction. The readout is given by the fluorescence of a single microsphere brought under the field of an epifluorescent microscope with a micro-manipulator, therefore limited in throughput and multiplexing. Recently, Jung et al. adapted the Catalytic Hairpin Assembly to the surface of microparticle (NPL 51). In this case again, the DNA strands at the surface of the particle are of only one type, and act as passive substrate (fuel molecule) allowing a diffusing DNA walker (catalyst strand) to move along the surface. Conversely, in the invention described herein, templates strands (modules) are bound to the microsphere allowing the on-site fabrication of short DNA strands using fuel molecules (dNTPs). Another fundamental difference is that the catalytic reaction in Jung et al. is mediated via non-enzymatic processes while CompuSpheres require to be contacted with an enzymatic machinery that performs the computation.

Regarding nucleic acid detection, current methods include Northern blotting, microarrays, sequencing and a variety of amplification-based methods (discussed below). Northern blotting, still widely used in academic research, is a separative technique that suffers from a lack of sensitivity and is not compatible with clinical applications due to tedious protocols, which induce a radiolabelling step. Microarrays appear as an alternative detection system due to their high parallelization capacity, however, they remain expensive and suffer from a lack of specificity since they mostly rely on the hybridization of target sequences to high packed immobilized capture oligonucleotides. Also microarrays are not sensitive enough for the detection of low levels of targets.

The polymerase chain reaction (PCR) is a molecular biology technique based upon target amplification through temperature cycles. This highly sensitive method allows to create millions copies of a target DNA strand from a few initial molecules. Its real-time implementation, named qPCR is the current standard for clinical detection of sequence and mutations. However, it may suffer from a lack of specificity due to nonspecific binding of primers and extension of non-perfect primer-template duplexes, resulting in the amplification of the wrong sequence. qPCR protocols, especially in multiplex format, are case-specific and need individual optimization to reach very low sensitivity. Additionally, PCR requires temperature cycling, primers design and, in the case of RNA detection, conversion of the RNA target to a usable DNA equivalent by a reverse transcription step, which may introduce biases.

Isothermal amplification-based techniques offer a simpler alternative to PCR and avoid the temperature cycling requirement. However, they are often affected by background due to unspecific amplification. As a result, the time-window where the small target concentration has already led to detectable signal, whereas the unspecific reaction has not yet produced signal, is typically very limited. Therefore real-time monitoring is required and end-point measurement (most convenient readout technique for diagnostic purposes) remains challenging. In particular if multiple samples have to be analyzed simultaneously, it can be very problematic to respect a very precise timing of the assay. Moreover, the most sensitive of those techniques, such as LAMP, require complex primer design and are difficult to multiplex.

As demonstrated here, programmed particles can totally solve the unspecific amplification issue thanks to the possibility to make the system bistable, or nearly bistable, using a plurality of encoding DNA strand. Therefore background amplification can be completely removed. The present embodiment demonstrates that, in absence of target, programmed particles remain indefinitely in their OFF state. As a consequence end-point measurements, challenging with previous methods, are now possible.

Having a highly available multiplex/parallel assay is becoming of paramount importance in cancer diagnosis.

As described above, in the present embodiment, it is shown that the molecular program can be run locally by attaching the mixture of DNA instructions on a solid microsphere. In particular, mixtures of DNA strands (instructions) are attached to microscopic beads to obtain storable, reusable and programmed beads which are able to perform predefined molecular programs when immerged in a solution containing the necessary enzymes, cofactors, fuel and input molecules. Because the programs run locally, it is now possible to perform identical but independent functions in parallel, at different locations in the same solution. This can bring significant decrease in reagent cost. It is also possible to perform many different functions, by using beads that have previously been programmed with different sets of DNA instructions and then pooled together. In this case, each type of bead can have a different barcode (e.g. a specific set of fluorescent labels) that allows the identification of the program it carries.

The disclosure in this Description is not limited to the above embodiment, but may be diversely modified and varied. Thus, the modifications and variations are not excluded from the scope of protection of the Claim(s) attached hereto.

INDUSTRIAL APPLICABILITY

The present invention is applicable to a molecular computing component and a method of molecular computing.

The invention claimed is:

1. A component for detection of molecular targets, the component comprising:
   a microsphere including pores, at least some of which are open on a surface of the microsphere, and
   a plurality of modules attached to the microsphere wherein each of the modules is a continuous sequence of nucleic acid bases, and multiple copies of each of the modules are attached to the microsphere,
   wherein the modules include a first and a second module, the first module is an amplification template and includes a partial repeat structure and a nicking enzyme recognition site, and the second module is a leak absorption template having a nucleic acid sequence, a 3' end that is complementary to a sequence amplified by the amplification template and a 5' end that is a sequence tail of one to six nucleotides, and
   wherein the modules include a target-conversion module as a third module having a nucleic acid sequence, a 5' end that is at least partially complementary to the amplified sequence, a nicking enzyme recognition site and a 3' end that is complementary to a target nucleic acid sequence.

2. The component according to claim 1, wherein the plurality of modules attached on the microsphere locally cooperate to sense chemical signals in their environment, compute a response and generate a reporting signal.

3. The component according to claim 2, wherein the component comprises a plurality of the microspheres, and the microspheres concurrently exist in an identical sample.

4. The component according to claim 3, wherein the microspheres are of different types, and each of the microspheres has a distinct combination of modules, thereby each of the microspheres performs a different sensing function.

5. The component according to claim 4, wherein the different types of microspheres can be distinguished by fluorescent labels grafted thereon.

6. The component according to claim 1, wherein a sensing function is performed cooperatively by a combination of the modules attached to the microsphere, the modules cooperate on the microsphere through exchanges of short DNA strands and independent functioning of microspheres is obtained without requirement of physical compartments.

7. The component according to claim 1, wherein the component comprises a plurality of the microspheres, each of the microspheres performs its sensing function independently in a unique solution.

8. The component according to claim 1 wherein at least one of the modules include a reporter.

9. The component according to claim 1, wherein at least one of the modules include a fluorescent label.

10. The component according to claim 1, wherein at least one of the modules has one or more biotin modification at one extremity, the microsphere is coated with streptavidin, and the module is immobilized on the microsphere via biotin-streptavidin linkage.

11. The component according to claim 1, wherein at least one of the modules bears other modifications selected from the group consisting of linkers, spacers, exonuclease-protecting modifications, fluorescent modifications, nucleobase modifications and backbone modifications.

12. The component according to claim 1, wherein the microsphere is made of hydrogel.

* * * * *